US 9,014,819 B2

(12) United States Patent
Lee et al.

(10) Patent No.: US 9,014,819 B2
(45) Date of Patent: *Apr. 21, 2015

(54) AUTONOMIC AROUSAL DETECTION SYSTEM AND METHOD

(71) Applicant: Cardiac Pacemakers, Inc., St. Paul, MN (US)

(72) Inventors: Kent Lee, Shoreview, MN (US); Quan Ni, Shoreview, MN (US); Jesse W. Hartley, Lake Elmo, MN (US); Jeffrey E. Stahmann, Ramsey, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/077,524

(22) Filed: Nov. 12, 2013

(65) Prior Publication Data

US 2014/0107506 A1 Apr. 17, 2014

Related U.S. Application Data

(63) Continuation of application No. 10/920,675, filed on Aug. 17, 2004, now Pat. No. 8,606,356.

(60) Provisional application No. 60/504,344, filed on Sep. 18, 2003.

(51) Int. Cl.
*A61N 1/00* (2006.01)
*A61N 1/36* (2006.01)
(Continued)

(52) U.S. Cl.
CPC .......... *A61N 1/36135* (2013.01); *A61B 5/0809* (2013.01); *A61B 5/113* (2013.01);
(Continued)

(58) Field of Classification Search
CPC .... A61B 5/0809; A61B 5/113; A61B 5/4519; A61B 5/4806; A61B 5/4809; A61M 16/0051; A61M 16/06; A61M 2205/054; A61M 2205/3569; A61M 2205/3592; A61M 2230/04; A61M 2230/10; A61M 2230/60; A61M 2230/63; A61N 1/3601; A61N 1/36135; A61N 1/362; A61N 1/36514; A61N 1/0051; A61N 1/0553; A61N 1/0558
USPC .......................................................... 607/116
See application file for complete search history.

(56) References Cited

U.S. PATENT DOCUMENTS 3,309,924 A  3/1967  Kohn et al.
3,522,811 A  8/1970  Schwartz et al.
(Continued)

FOREIGN PATENT DOCUMENTS

EP   0547734 A2   6/1993
EP   0750920 A1   1/1997
(Continued)

OTHER PUBLICATIONS

Bradley et al., Sleep Apnea and Heart Failure, Park I:Obstrutive Sleep Apnea, 107 Circulation 1671-1678 (2003).
(Continued)

*Primary Examiner* — George Manuel
(74) *Attorney, Agent, or Firm* — Seager, Tufte & Wickhem, LLC

(57) ABSTRACT

Various approaches to detecting arousals from sleep involve generating signals modulated by muscle tone, brainwave activity, and/or other nervous system activity associated with a patient's autonomic arousal response. Generating the signals and/or detecting autonomic arousals from sleep may be performed using an implantable device. Arousal information may be useful to identify sleep disorder events associated with arousals from sleep, for diagnostic purposes, and/or for therapy adjustment.

20 Claims, 20 Drawing Sheets

(51) Int. Cl.
   *A61B 5/08*       (2006.01)
   *A61B 5/113*      (2006.01)
   *A61M 16/00*      (2006.01)
   *A61N 1/365*      (2006.01)
   *A61B 5/00*       (2006.01)
   *A61M 16/06*      (2006.01)
   *A61N 1/362*      (2006.01)

(52) U.S. Cl.
   CPC ............ *A61B 5/4519* (2013.01); *A61B 5/4806* (2013.01); *A61B 5/4809* (2013.01); *A61M 16/0051* (2013.01); *A61M 16/06* (2013.01); *A61M 2205/054* (2013.01); *A61M 2205/3569* (2013.01); *A61M 2205/3592* (2013.01); *A61M 2230/04* (2013.01); *A61M 2230/10* (2013.01); *A61M 2230/60* (2013.01); *A61M 2230/63* (2013.01); *A61N 1/3601* (2013.01); *A61N 1/362* (2013.01); *A61N 1/36514* (2013.01)

(56) References Cited

U.S. PATENT DOCUMENTS

| | | | |
|---|---|---|---|
| 3,650,277 | A | 3/1972 | Sjostrand et al. |
| 3,835,864 | A | 9/1974 | Rasor et al. |
| 3,870,051 | A | 3/1975 | Brindley |
| 3,943,936 | A | 3/1976 | Rasor et al. |
| 4,312,734 | A | 1/1982 | Nichols |
| 4,323,073 | A | 4/1982 | Ferris |
| 4,365,636 | A | 12/1982 | Barker et al. |
| 4,390,405 | A | 6/1983 | Hahn et al. |
| 4,562,841 | A | 1/1986 | Brockway et al. |
| 4,573,481 | A | 3/1986 | Bullara et al. |
| 4,590,946 | A | 5/1986 | Loeb et al. |
| 4,702,253 | A | 10/1987 | Nappholz et al. |
| 4,719,921 | A | 1/1988 | Chirife |
| 4,721,110 | A | 1/1988 | Lampadius |
| 4,777,962 | A | 10/1988 | Watson et al. |
| 4,784,162 | A | 11/1988 | Ricks et al. |
| 4,791,931 | A | 12/1988 | Slate |
| 4,802,485 | A | 2/1989 | Bowers et al. |
| 4,807,629 | A | 2/1989 | Baudino et al. |
| 4,813,427 | A | 3/1989 | Schlaefke et al. |
| 4,819,662 | A | 4/1989 | Heil et al. |
| 4,827,935 | A | 5/1989 | Geddes et al. |
| 4,827,943 | A | 5/1989 | Bornn et al. |
| 4,830,008 | A | 5/1989 | Meer |
| 4,836,219 | A | 6/1989 | Hobson et al. |
| 4,846,195 | A | 7/1989 | Alt |
| 4,856,524 | A | 8/1989 | Baker |
| 4,875,477 | A | 10/1989 | Waschke et al. |
| 4,886,064 | A | 12/1989 | Strandberg |
| 4,928,688 | A | 5/1990 | Mower |
| 4,940,065 | A | 7/1990 | Tanagho et al. |
| 4,953,551 | A | 9/1990 | Mehra et al. |
| 4,958,632 | A | 9/1990 | Duggan et al. |
| 4,960,129 | A | 10/1990 | dePaola et al. |
| 4,961,423 | A | 10/1990 | Canducci |
| 4,967,159 | A | 10/1990 | Manes |
| 4,972,842 | A | 11/1990 | Korten et al. |
| 4,972,848 | A | 11/1990 | Di Domenico et al. |
| 4,982,738 | A | 1/1991 | Griebel |
| 5,010,888 | A | 4/1991 | Jadvar et al. |
| 5,024,222 | A | 6/1991 | Thacker |
| 5,036,849 | A | 8/1991 | Hauck et al. |
| 5,040,533 | A | 8/1991 | Fearnot |
| 5,047,930 | A | 9/1991 | Martens et al. |
| 5,063,927 | A | 11/1991 | Webb et al. |
| 5,105,354 | A | 4/1992 | Nishimura et al. |
| 5,111,815 | A | 5/1992 | Mower |
| 5,123,425 | A | 6/1992 | Shannon et al. |
| 5,133,353 | A | 7/1992 | Hauser |
| 5,144,960 | A | 9/1992 | Mehra et al. |
| 5,146,918 | A | 9/1992 | Kallok |
| 5,156,157 | A | 10/1992 | Valenta et al. |
| 5,170,784 | A | 12/1992 | Ramon |
| 5,174,287 | A | 12/1992 | Kallok |
| 5,178,156 | A | 1/1993 | Takishima et al. |
| 5,179,945 | A | 1/1993 | Van Hofwegen et al. |
| 5,183,038 | A | 2/1993 | Hoffman et al. |
| 5,187,657 | A | 2/1993 | Forbes et al. |
| 5,188,106 | A | 2/1993 | Nappholz et al. |
| 5,190,035 | A | 3/1993 | Salo |
| 5,199,424 | A | 4/1993 | Sullivan et al. |
| 5,199,428 | A | 4/1993 | Obel et al. |
| 5,203,326 | A | 4/1993 | Collins et al. |
| 5,203,348 | A | 4/1993 | Dahl et al. |
| 5,209,229 | A | 5/1993 | Gilli et al. |
| 5,211,173 | A | 5/1993 | Kallok et al. |
| 5,215,082 | A | 6/1993 | Kallok et al. |
| 5,215,089 | A | 6/1993 | Baker et al. |
| 5,230,337 | A | 7/1993 | Dahl et al. |
| 5,233,983 | A | 8/1993 | Markowitz |
| 5,243,979 | A | 9/1993 | Stein |
| 5,243,980 | A | 9/1993 | Mehra |
| 5,245,995 | A | 9/1993 | Sullivan et al. |
| 5,259,373 | A | 11/1993 | Gruenke et al. |
| 5,261,400 | A | 11/1993 | Bardy |
| 5,275,159 | A | 1/1994 | Griebel |
| 5,280,791 | A | 1/1994 | Lavie |
| 5,282,468 | A | 2/1994 | Klepinski et al. |
| 5,284,136 | A | 2/1994 | Hauck et al. |
| 5,292,338 | A | 3/1994 | Bardy |
| 5,299,118 | A | 3/1994 | Martens et al. |
| 5,300,106 | A | 4/1994 | Dahl et al. |
| 5,301,677 | A | 4/1994 | Hsung |
| 5,313,953 | A | 5/1994 | Yomtov et al. |
| 5,314,430 | A | 5/1994 | Bardy |
| 5,314,459 | A | 5/1994 | Swanson et al. |
| 5,318,592 | A | 6/1994 | Schaldach |
| 5,318,597 | A | 6/1994 | Hauck |
| 5,330,505 | A | 7/1994 | Cohen |
| 5,330,507 | A | 7/1994 | Schwartz et al. |
| 5,330,515 | A | 7/1994 | Rutecki et al. |
| 5,331,966 | A | 7/1994 | Bennett et al. |
| 5,334,221 | A | 8/1994 | Bardy |
| 5,334,222 | A | 8/1994 | Salo et al. |
| 5,335,647 | A | 8/1994 | Brustad |
| 5,335,657 | A | 8/1994 | Terry, Jr. et al. |
| 5,351,394 | A | 10/1994 | Weinberg et al. |
| 5,356,425 | A | 10/1994 | Bardy |
| 5,360,442 | A | 11/1994 | Dahl et al. |
| 5,363,842 | A | 11/1994 | Mishelevich et al. |
| 5,366,496 | A | 11/1994 | Dahl et al. |
| 5,372,606 | A | 12/1994 | Lang |
| 5,376,106 | A | 12/1994 | Stahmann |
| 5,376,476 | A | 12/1994 | Eylon et al. |
| 5,388,578 | A | 2/1995 | Yomtov et al. |
| 5,391,200 | A | 2/1995 | KenKnight |
| 5,397,342 | A | 3/1995 | Heil et al. |
| 5,398,682 | A | 3/1995 | Lynn et al. |
| 5,404,877 | A | 4/1995 | Nolan et al. |
| 5,411,031 | A | 5/1995 | Yomtov et al. |
| 5,411,525 | A | 5/1995 | Swanson et al. |
| 5,411,531 | A | 5/1995 | Hill et al. |
| 5,411,539 | A | 5/1995 | Neisz et al. |
| 5,411,540 | A | 5/1995 | Edell et al. |
| 5,437,285 | A | 8/1995 | Verrier et al. |
| 5,439,482 | A | 8/1995 | Adams et al. |
| 5,441,518 | A | 8/1995 | Adams et al. |
| 5,466,245 | A | 11/1995 | Spinelli et al. |
| 5,468,254 | A | 11/1995 | Hahn et al. |
| 5,483,969 | A | 1/1996 | Testerman et al. |
| 5,485,851 | A | 1/1996 | Erickson |
| 5,487,755 | A | 1/1996 | Snell et al. |
| 5,507,784 | A | 4/1996 | Hill |
| 5,520,176 | A | 5/1996 | Cohen et al. |
| 5,522,382 | A | 6/1996 | Sullivan et al. |
| 5,522,854 | A | 6/1996 | Ideker et al. |
| 5,522,862 | A | 6/1996 | Testerman et al. |
| 5,531,779 | A | 7/1996 | Dahl et al. |
| 5,540,727 | A | 7/1996 | Tockman et al. |
| 5,540,734 | A | 7/1996 | Zabara |
| 5,540,735 | A | 7/1996 | Wingrove |

(56) References Cited

U.S. PATENT DOCUMENTS

| | | |
|---|---|---|
| 5,545,186 A | 8/1996 | Olson et al. |
| 5,545,202 A | 8/1996 | Dahl et al. |
| 5,549,655 A | 8/1996 | Erickson et al. |
| 5,571,150 A | 11/1996 | Wernicke et al. |
| 5,578,061 A | 11/1996 | Stroetmann et al. |
| 5,590,648 A | 1/1997 | Mitchell et al. |
| 5,591,216 A | 1/1997 | Testerman et al. |
| 5,593,431 A | 1/1997 | Sheldon |
| 5,603,732 A | 2/1997 | Dahl et al. |
| 5,605,151 A | 2/1997 | Lynn et al. |
| 5,606,969 A | 3/1997 | Butler et al. |
| 5,620,466 A | 4/1997 | Haefner et al. |
| 5,622,178 A | 4/1997 | Gilham |
| 7,010,337 B2 | 3/2006 | Furnary et al. |
| 7,010,345 B2 | 3/2006 | Hill et al. |
| 7,025,729 B2 | 4/2006 | de Chazal et al. |
| 7,043,305 B2 | 5/2006 | KenKnight et al. |
| 7,050,851 B2 | 5/2006 | Plombon et al. |
| 7,062,308 B1 | 6/2006 | Jackson |
| 7,065,407 B2 | 6/2006 | Bardy et al. |
| 7,065,409 B2 | 6/2006 | Mazar |
| 7,065,410 B2 | 6/2006 | Bardy et al. |
| 7,069,080 B2 | 6/2006 | Bardy et al. |
| 7,072,720 B2 | 7/2006 | Puskas |
| 7,076,296 B2 | 7/2006 | Rissmann et al. |
| 7,089,936 B2 | 8/2006 | Madaus et al. |
| 7,090,682 B2 | 8/2006 | Sanders et al. |
| 7,092,754 B2 | 8/2006 | Bardy et al. |
| 7,092,755 B2 | 8/2006 | Florio |
| 7,101,341 B2 | 9/2006 | Tsukashima et al. |
| 7,117,036 B2 | 10/2006 | Florio |
| 7,120,495 B2 | 10/2006 | Bardy et al. |
| 7,123,959 B2 | 10/2006 | Cates |
| 7,127,290 B2 | 10/2006 | Girouard et al. |
| 7,127,300 B2 | 10/2006 | Mazar et al. |
| 7,130,687 B2 | 10/2006 | Cho et al. |
| 7,136,704 B2 | 11/2006 | Schulman |
| 7,142,917 B2 | 11/2006 | Fukui |
| 7,146,212 B2 | 12/2006 | Bardy et al. |
| 7,149,574 B2 | 12/2006 | Yun et al. |
| 7,149,575 B2 | 12/2006 | Ostroff et al. |
| 7,155,278 B2 | 12/2006 | King et al. |
| 7,155,284 B1 | 12/2006 | Whitehurst et al. |
| 7,158,832 B2 | 1/2007 | Kieval et al. |
| 7,162,303 B2 | 1/2007 | Levin et al. |
| 7,168,429 B2 | 1/2007 | Matthews et al. |
| 7,184,817 B2 | 2/2007 | Zhu et al. |
| 7,189,204 B2 | 3/2007 | Ni et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,204,805 B2 | 4/2007 | Dean |
| 7,206,635 B2 | 4/2007 | Cho et al. |
| 7,207,945 B2 | 4/2007 | Bardy |
| 7,212,862 B2 | 5/2007 | Park et al |
| 7,218,964 B2 | 5/2007 | Hill et al. |
| 7,225,013 B2 | 5/2007 | Geva et al. |
| 7,225,809 B1 | 6/2007 | Bowen et al. |
| 7,231,250 B2 | 6/2007 | Band et al. |
| 7,235,050 B2 | 6/2007 | Schulman et al. |
| 7,245,971 B2 | 7/2007 | Park et al. |
| 7,252,640 B2 | 8/2007 | Ni et al. |
| 7,258,670 B2 | 8/2007 | Bardy |
| 7,269,459 B1 | 9/2007 | Koh |
| 7,277,757 B2 | 10/2007 | Casavant et al. |
| 7,277,761 B2 | 10/2007 | Shelchuk |
| 7,292,890 B2 | 11/2007 | Whitehurst et al. |
| 7,302,295 B2 | 11/2007 | Stahmann et al. |
| 7,305,265 B2 | 12/2007 | Fukui |
| 7,308,311 B2 | 12/2007 | Sorensen et al. |
| 7,310,552 B2 | 12/2007 | Puskas |
| 7,314,046 B2 | 1/2008 | Schroeder et al. |
| 7,363,076 B2 | 4/2008 | Yun et al. |
| 7,366,572 B2 | 4/2008 | Heruth et al. |
| 7,376,463 B2 | 5/2008 | Salo et al. |
| 7,390,038 B2 | 6/2008 | Campbell et al. |
| 7,396,333 B2 | 7/2008 | Stahmann et al. |
| 7,400,928 B2 | 7/2008 | Hatlestsad |
| 7,413,549 B1 | 8/2008 | Koh |
| 7,425,200 B2 | 9/2008 | Brockway et al. |
| 7,428,468 B2 | 9/2008 | Takemura et al. |
| 7,435,221 B1 | 10/2008 | Bharmi et al. |
| 7,438,686 B2 | 10/2008 | Cho et al. |
| 7,440,795 B2 | 10/2008 | Poezevara |
| 7,445,601 B2 | 11/2008 | Kline |
| 7,460,906 B2 | 12/2008 | Libbus |
| 7,469,697 B2 | 12/2008 | Lee et al. |
| 7,481,759 B2 | 1/2009 | Whitehurst et al. |
| 7,486,991 B2 | 2/2009 | Libbus et al. |
| 7,499,742 B2 | 3/2009 | Bolea et al. |
| 7,509,164 B2 | 3/2009 | Jensen et al. |
| 7,509,166 B2 | 3/2009 | Libbus |
| 7,515,969 B2 | 4/2009 | Tockman et al. |
| 7,542,800 B2 | 6/2009 | Libbus et al. |
| 7,570,999 B2 | 8/2009 | Libbus et al. |
| 7,587,238 B2 | 9/2009 | Moffitt et al. |
| 7,616,990 B2 | 11/2009 | Chavan et al. |
| 7,616,997 B2 | 11/2009 | Kieval et al. |
| 7,623,926 B2 | 11/2009 | Rossing et al. |
| 7,634,317 B2 | 12/2009 | Ben-David et al. |
| 7,643,875 B2 | 1/2010 | Heil, Jr. et al. |
| 7,657,312 B2 | 2/2010 | Pastore et al. |
| 7,660,628 B2 | 2/2010 | Libbus et al. |
| 7,662,101 B2 | 2/2010 | Lee et al. |
| 7,664,546 B2 | 2/2010 | Hartley et al. |
| 7,678,061 B2 | 3/2010 | Lee et al. |
| 7,680,537 B2 | 3/2010 | Stahmann et al. |
| 7,689,276 B2 | 3/2010 | Dobak |
| 7,706,884 B2 | 4/2010 | Libbus |
| 7,720,541 B2 | 5/2010 | Stahmann et al. |
| 7,738,967 B2 | 6/2010 | Salo |
| 7,747,323 B2 | 6/2010 | Libbus et al. |
| 7,766,842 B2 | 8/2010 | Ni et al. |
| 7,769,450 B2 | 8/2010 | Libbus et al. |
| 7,778,703 B2 | 8/2010 | Gross et al. |
| 7,778,711 B2 | 8/2010 | Ben-David et al. |
| 7,785,323 B2 | 8/2010 | Jenkins et al. |
| 7,840,266 B2 | 11/2010 | Libbus et al. |
| 7,869,881 B2 | 1/2011 | Libbus et al. |
| 7,930,038 B2 | 4/2011 | Zarembo |
| 7,970,470 B2 | 6/2011 | Hartley et al. |
| 8,002,553 B2 | 8/2011 | Hatlestad et al. |
| 8,024,050 B2 | 9/2011 | Libbus et al. |
| 8,046,069 B2 | 10/2011 | Kramer et al. |
| 8,126,559 B2 | 2/2012 | Libbus |
| 8,126,560 B2 | 2/2012 | Scheiner et al. |
| 8,152,732 B2 | 4/2012 | Lynn et al. |
| 8,175,705 B2 | 5/2012 | Libbus |
| 8,192,376 B2 | 6/2012 | Lovett et al. |
| 8,396,560 B2 | 3/2013 | Libbus et al. |
| 8,417,334 B2 | 4/2013 | Hill et al. |
| 8,535,222 B2 | 9/2013 | Ni et al. |
| 8,606,356 B2 | 12/2013 | Lee et al. |
| 8,640,698 B2 | 2/2014 | Darkin et al. |
| 2002/0005982 A1 | 1/2002 | Borlinghaus |
| 2002/0026222 A1 | 2/2002 | Schauerte et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0058877 A1 | 5/2002 | Baumann |
| 2002/0068897 A1 | 6/2002 | Jenkins et al. |
| 2002/0068958 A1 | 6/2002 | Bardy et al. |
| 2002/0072773 A1 | 6/2002 | Bardy et al. |
| 2002/0072776 A1 | 6/2002 | Osorio et al. |
| 2002/0082652 A1 | 6/2002 | Wentkowski et al. |

(56) References Cited

U.S. PATENT DOCUMENTS

| | | |
|---|---|---|
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0103516 A1 | 8/2002 | Patwardhan et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |
| 2002/0128700 A1 | 9/2002 | Cross, Jr. |
| 2002/0143264 A1 | 10/2002 | Ding et al. |
| 2002/0143369 A1 | 10/2002 | Hill et al. |
| 2002/0151051 A1 | 10/2002 | Li |
| 2002/0161410 A1 | 10/2002 | Kramer et al. |
| 2002/0165462 A1 | 11/2002 | Westbrook et al. |
| 2002/0169485 A1 | 11/2002 | Pless et al. |
| 2002/0183237 A1 | 12/2002 | Puskas |
| 2002/0193685 A1 | 12/2002 | Mate et al. |
| 2002/0193839 A1 | 12/2002 | Cho et al. |
| 2002/0198570 A1 | 12/2002 | Puskas |
| 2003/0003052 A1 | 1/2003 | Hampton |
| 2003/0004546 A1 | 1/2003 | Casey |
| 2003/0004549 A1 | 1/2003 | Hill et al. |
| 2003/0004552 A1 | 1/2003 | Plombon |
| 2003/0023175 A1 | 1/2003 | Arzbaecher et al. |
| 2003/0023184 A1 | 1/2003 | Pitts-Crick et al. |
| 2003/0023279 A1 | 1/2003 | Spinelli |
| 2003/0036773 A1 | 2/2003 | Whitehurst et al. |
| 2003/0036778 A1 | 2/2003 | Ostroff et al. |
| 2003/0045904 A1 | 3/2003 | Bardy et al. |
| 2003/0045909 A1 | 3/2003 | Gross et al. |
| 2003/0045914 A1 | 3/2003 | Cohen et al. |
| 2003/0050538 A1 | 3/2003 | Naghavi et al. |
| 2003/0055461 A1 | 3/2003 | Girouard et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0069609 A1 | 4/2003 | Thompson |
| 2003/0073919 A1 | 4/2003 | Hampton et al. |
| 2003/0074039 A1 | 4/2003 | Puskas |
| 2003/0078629 A1 | 4/2003 | Chen |
| 2003/0083241 A1 | 5/2003 | Young |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0100924 A1 | 5/2003 | Foreman et al. |
| 2003/0100925 A1 | 5/2003 | Pape |
| 2003/0105493 A1 | 6/2003 | Salo |
| 2003/0149450 A1 | 8/2003 | Mayberg |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0171791 A1 | 9/2003 | KenKnight et al. |
| 2003/0178031 A1 | 9/2003 | Du Pen et al. |
| 2003/0181951 A1 | 9/2003 | Cates |
| 2003/0195571 A1 | 10/2003 | Burnes et al. |
| 2003/0195578 A1 | 10/2003 | Perron et al. |
| 2003/0199945 A1 | 10/2003 | Ciulla |
| 2003/0204213 A1 | 10/2003 | Jensen et al. |
| 2003/0212436 A1 | 11/2003 | Brown |
| 2003/0212440 A1 | 11/2003 | Boveja |
| 2003/0216789 A1 | 11/2003 | Deem et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0002742 A1 | 1/2004 | Florio |
| 2004/0019364 A1 | 1/2004 | Kieval et al. |
| 2004/0030362 A1 | 2/2004 | Hill et al. |
| 2004/0059240 A1 | 3/2004 | Cho et al. |
| 2004/0073093 A1 | 4/2004 | Hatlestad |
| 2004/0088027 A1 | 5/2004 | Burnes et al. |
| 2004/0102814 A1 | 5/2004 | Sorensen et al. |
| 2004/0122487 A1 | 6/2004 | Hatlestad et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0172074 A1 | 9/2004 | Yoshihito |
| 2004/0176809 A1 | 9/2004 | Cho et al. |
| 2004/0193231 A1 | 9/2004 | David et al. |
| 2004/0210154 A1 | 10/2004 | Kline |
| 2004/0210261 A1 | 10/2004 | King et al. |
| 2004/0215240 A1 | 10/2004 | Lovett et al. |
| 2004/0215289 A1 | 10/2004 | Fukui |
| 2004/0230229 A1 | 11/2004 | Lovett et al. |
| 2004/0230230 A1 | 11/2004 | Lindstrom et al. |
| 2004/0249299 A1 | 12/2004 | Cobb |
| 2004/0249416 A1 | 12/2004 | Yun et al. |
| 2004/0254616 A1 | 12/2004 | Rossing et al. |
| 2005/0004615 A1 | 1/2005 | Sanders |
| 2005/0021092 A1 | 1/2005 | Yun et al. |
| 2005/0039745 A1 | 2/2005 | Stahmann et al. |
| 2005/0042589 A1 | 2/2005 | Hatlestad et al. |
| 2005/0043772 A1 | 2/2005 | Stahmann et al. |
| 2005/0065447 A1 | 3/2005 | Lee et al. |
| 2005/0065567 A1 | 3/2005 | Lee et al. |
| 2005/0065572 A1 | 3/2005 | Hartley et al. |
| 2005/0065575 A1 | 3/2005 | Dobak |
| 2005/0076908 A1* | 4/2005 | Lee et al. .................. 128/204.23 |
| 2005/0085864 A1 | 4/2005 | Schulman et al. |
| 2005/0093581 A1 | 5/2005 | Kang |
| 2005/0096705 A1 | 5/2005 | Pastore et al. |
| 2005/0101841 A9 | 5/2005 | Kaylor et al. |
| 2005/0107838 A1 | 5/2005 | Lovett et al. |
| 2005/0119711 A1 | 6/2005 | Cho et al. |
| 2005/0131467 A1 | 6/2005 | Boveja |
| 2005/0137645 A1 | 6/2005 | Voipio et al. |
| 2005/0142070 A1 | 6/2005 | Hartley et al. |
| 2005/0143779 A1 | 6/2005 | Libbus |
| 2005/0143787 A1 | 6/2005 | Boveja et al. |
| 2005/0145246 A1 | 7/2005 | Hartley et al. |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0149752 A1 | 7/2005 | Johnson et al. |
| 2005/0159784 A1 | 7/2005 | Arceta |
| 2005/0197675 A1 | 9/2005 | David et al. |
| 2005/0288728 A1 | 12/2005 | Libbus et al. |
| 2006/0047333 A1 | 3/2006 | Tockman |
| 2006/0079945 A1 | 4/2006 | Libbus |
| 2006/0106428 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0195041 A1 | 8/2006 | Lynn et al. |
| 2006/0206153 A1 | 9/2006 | Libbus et al. |
| 2006/0206154 A1 | 9/2006 | Moffitt et al. |
| 2006/0217772 A1 | 9/2006 | Libbus et al. |
| 2006/0224188 A1 | 10/2006 | Libbus et al. |
| 2006/0293714 A1 | 12/2006 | Salo et al. |
| 2007/0038278 A1 | 2/2007 | Zarembo |
| 2007/0055115 A1 | 3/2007 | Kwok et al. |
| 2007/0093875 A1 | 4/2007 | Chavan et al. |
| 2007/0112388 A1 | 5/2007 | Salo |
| 2007/0142871 A1 | 6/2007 | Libbus et al. |
| 2007/0149860 A1 | 6/2007 | Lynn et al. |

(56) References Cited

U.S. PATENT DOCUMENTS

| | | | |
|---|---|---|---|
| 2007/0150014 A1 | 6/2007 | Kramer et al. |
| 2007/0161873 A1 | 7/2007 | Ni et al. |
| 2007/0185542 A1 | 8/2007 | Bolea et al. |
| 2007/0282215 A1 | 12/2007 | Ni et al. |
| 2008/0045813 A1 | 2/2008 | Phuah et al. |
| 2009/0007918 A1 | 1/2009 | Darkin et al. |

FOREIGN PATENT DOCUMENTS

| | | | |
|---|---|---|---|
| EP | 0770407 A1 | 5/1997 |
| EP | 0940155 A2 | 9/1999 |
| EP | 1151718 A2 | 11/2001 |
| EP | 1162125 A2 | 12/2001 |
| EP | 1172125 A1 | 1/2002 |
| EP | 1317943 A1 | 6/2003 |
| EP | 1486232 A2 | 12/2004 |
| EP | 1541193 A1 | 6/2005 |
| JP | 2002519161 A | 7/2002 |
| WO | 8402080 A1 | 6/1984 |
| WO | 9203983 A1 | 3/1992 |
| WO | 9220402 A1 | 11/1992 |
| WO | 9301862 A1 | 2/1993 |
| WO | 9718856 A1 | 5/1997 |
| WO | 9904841 A1 | 2/1999 |
| WO | 0001438 A1 | 1/2000 |
| WO | 0017615 A2 | 3/2000 |
| WO | 0100273 A1 | 1/2001 |
| WO | 0124876 A1 | 4/2001 |
| WO | 0176689 A2 | 10/2001 |
| WO | 0226318 A1 | 4/2002 |
| WO | 0234327 A2 | 5/2002 |
| WO | 0240096 A1 | 5/2002 |
| WO | 02085448 A2 | 10/2002 |
| WO | 02087433 A1 | 11/2002 |
| WO | 02087696 A1 | 11/2002 |
| WO | 03011388 A2 | 2/2003 |
| WO | 03041559 A2 | 5/2003 |
| WO | 03063954 A1 | 8/2003 |
| WO | 03075744 A2 | 9/2003 |
| WO | 03076008 A1 | 9/2003 |
| WO | 03082080 A2 | 10/2003 |
| WO | 03099373 A2 | 12/2003 |
| WO | 03099377 A1 | 12/2003 |
| WO | 2004012814 A1 | 2/2004 |
| WO | 2004062485 A2 | 7/2004 |
| WO | 2004084990 A1 | 10/2004 |
| WO | 2004084993 A1 | 10/2004 |
| WO | 2004103455 A2 | 12/2004 |
| WO | 2004105870 A1 | 12/2004 |
| WO | 2004110549 A2 | 12/2004 |
| WO | 2005018739 A1 | 3/2005 |
| WO | 2005028029 A2 | 3/2005 |
| WO | 2005042091 A1 | 5/2005 |
| WO | 2005053788 A1 | 6/2005 |
| WO | 2005063332 A1 | 7/2005 |
| WO | 2005065771 A1 | 7/2005 |
| WO | 2006031331 A1 | 3/2006 |

OTHER PUBLICATIONS

Garrigue et al., Benefit of Atrial Pacing in Sleep Apnea Syndrome, 346 N. Engl. J. Med. 404-412 (2002). Abstract only.
Hilton et al., Evaluation of Frequency and Time-frequency Spectral Analysis of Heart Rate Variability as a Diagnostic Marker of Sleep Apnea Syndrome, 37 Med. Biol. Eng. Comput. 760-769 (1999). Abstract only.
Javaheri et al., Sleep Apenea in S1 Ambulatory Male Patients with Stable Heart Failure: Types and Their Prevalences, Consequences, and Presentations, 97 Circulation 2154-2159 (1998).
Olusola et al., Nightcap: Laboratory and home-based evaluation of a portable sleep monitor, 32 Psychophysiology, 32-98 (1995). Abstract only.
Roche et al., Screening of Obstructive Sleep Apnea Syndrome by Heart Rate Variability Analysis, 100 Circulation 1411-1455 (1999).
Shahrokh. A Mechanism of Central Sleep Apnea in Patients With Heart Failure, 341 N. Engl. J. Med. 949-954 (1999). Abstract only.
Vannien et al., Cardiac Sympathovagal Balance During Sleep Apnea Episodes, 16 Clin. Physiol. 209-216 (1996). Abstract only.
Waldemark et al., Detection of Apnea using Short Window FFT Technique and Artificial Neural Network, 3390 SPIE International Society for Optical Engineering 122-133 (1998).
Young et al., The Occurrence of Sleep-Disordered Breathing Among Middle Aged Adults, N. Engl. J. Med. 1230-1235 (1993). Abstract only.
Balaban et al., Feasibility of Screening for Sleep Apnea Using Pacemaker Impedance Senser, NASPE 22nd Annual Scientific Sessions. Apr. 2001, vol. 24, No. 4, Part II, #313, 1 page, Abstract only.
Garrigue et al., Night Atrial Overdrive with DDD Pacing Results in a Significant Reduction of Sleep Apnea Episodes and QOI. Improvement in Heart Failure Patients, NASPE, 2001, 1 page, #145, Abstract only.
Garrigue et al., Night Atrial Overdrive with DDD Pacing: A New Therapy for Sleep Apnea Syndrome, NASPE 21st Annual Scientific Sessions, Apr. 2000, vol. 23, No. 4, Part II. #591, 1 page, Abstract only.
Verrier et al., Sleep, dreams, and sudden death: the case for sleep as an autonomic stress test for the heart, Cardiovascular Research 31 (1996) pp. 181-211.
Verrier et al., Sleep Related Cardiovascular Risk: New Home-Based Monitoring Technology for Improved Diagnosis and Therapy, from the Institute for Prevention of Cardiovascular Disease, Apr. 1997, pp. 158-175.
International Search Report dated Dec. 6, 2004 from PCT Application No. PCT/US2004/026883, 8 pages.
International Search Report dated Dec. 22, 2004 from PCT Application No. PCT/US2004/030787, 7 pages.
International Preliminary Report on Patentability from PCT Application No. PCT/US2004/030787, 9 pages.
Office Action dated Oct. 5, 2009 from Japanese Application No. 2004-557545, 3 pages.
Office Action (partial translation) dated Mar. 5, 2010 from Japanese Application No. 2004-557558, 3 pages.
Office Action dated May 31, 2010 from Japanese Application No. 2004-524027, 2 pages.
Office Action (partial translation) dated Jul. 28, 2010 from Japanese Application No. 2004-557558, 2 pages.
Office Action dated Aug. 2, 2010 from Japanese Application No. 2004-557545, 4 pages.
Office Action dated Dec. 13, 2010 from Japanese Application No. 2006-524027, 2 pages.
Office Action dated Jul. 11, 2011 from Japanese Application No. 2004-557545, 4 pages.
http://www.cardioconsult.com/Anatomy/, 2003.
Aircraft Noise and Sleep Disturbance: Final Report, prepared by the Civil Aviation Authority London on behalf of the Department of Trade, Aug. 1980 (CAA Report).
Andersen, Long-term Follow-up of Patients From a Randomized Trial of Atrial Versus Ventricular Pacing for Sick-Sinus Syndrome. Lancet, 350(9086), Oct. 25, 1997, 1210-6.
Altshule et al., The Effect of Position on Periodic Breathing in Chronic Cardiac Decomposition, New Engl. Journal of Med., vol. 259, No. 22. pp. 1064-1066. Nov. 27, 1958.
Benchimol, Cardiac Hemodynamics During Stimulation of the Right Atrium, Right Ventricle, and Left Ventricle in Normal and Abnormal Hearts, Circulation 33(6), Jun. 1966, 933-44.
Bevan et al., Postganglionic Sympathetic Delay in Vascular Delay in Vascular Smooth Muscle, Journal of Pharmacology & Experimental Therapeutics, 152(2), May 1966, 221-30.
Bevan et al., Sympathetic nerve-free vascular muscle. Journal of Pharmacology & Experimental Therapeutics, 157 (1), Jul. 1967, 117-24.
Bilgutay et al., A new concept in the treatment of hypertension utilizing an implantable electronic device: Baropacer. Trans. Am. Society Artificial Internal Organs. 1964. vol. 10, pp. 387-395.

(56) References Cited

OTHER PUBLICATIONS

Bilgutay, Vagal Tuning: A New Concept in the Treatment of Superventrical Arrhythmias, Agina Pectoris, and Heart Failure, Journal of Thoracic and Cardiovascular Surgery, 56(1), Jul. 1968, 71-82.

Bilgutay et al., Vagal tuning for the control of supraventricular arrhythmias. Surgical Forum, 16, 1965, 151-3.

Bolea et al., Preliminary Statement for Baroreflex Therapy for Disordered Breathing, Dec. 28, 2006, pp. 3.

Borst et al., Optimal Frequency of Carotid Sinus Nerve Stimulation in Treatment of Angina Pectoris, Cardiovascular Research, 8(5), Sep. 1974, 674-80.

Bradley et al., Cardiac Output Response to Continuous Positive Airway Pressure in Congestive Heart Failure, 145 Am. Rev. Respir. Dis. 377-382 (1992).

Bradley et al., Pathophysiologic and Therapeutic Implications of sleep apnia in Conjestive Heart Failure, 3J, Cardiac Failure 223-240 (1996) Abstract only.

\* cited by examiner

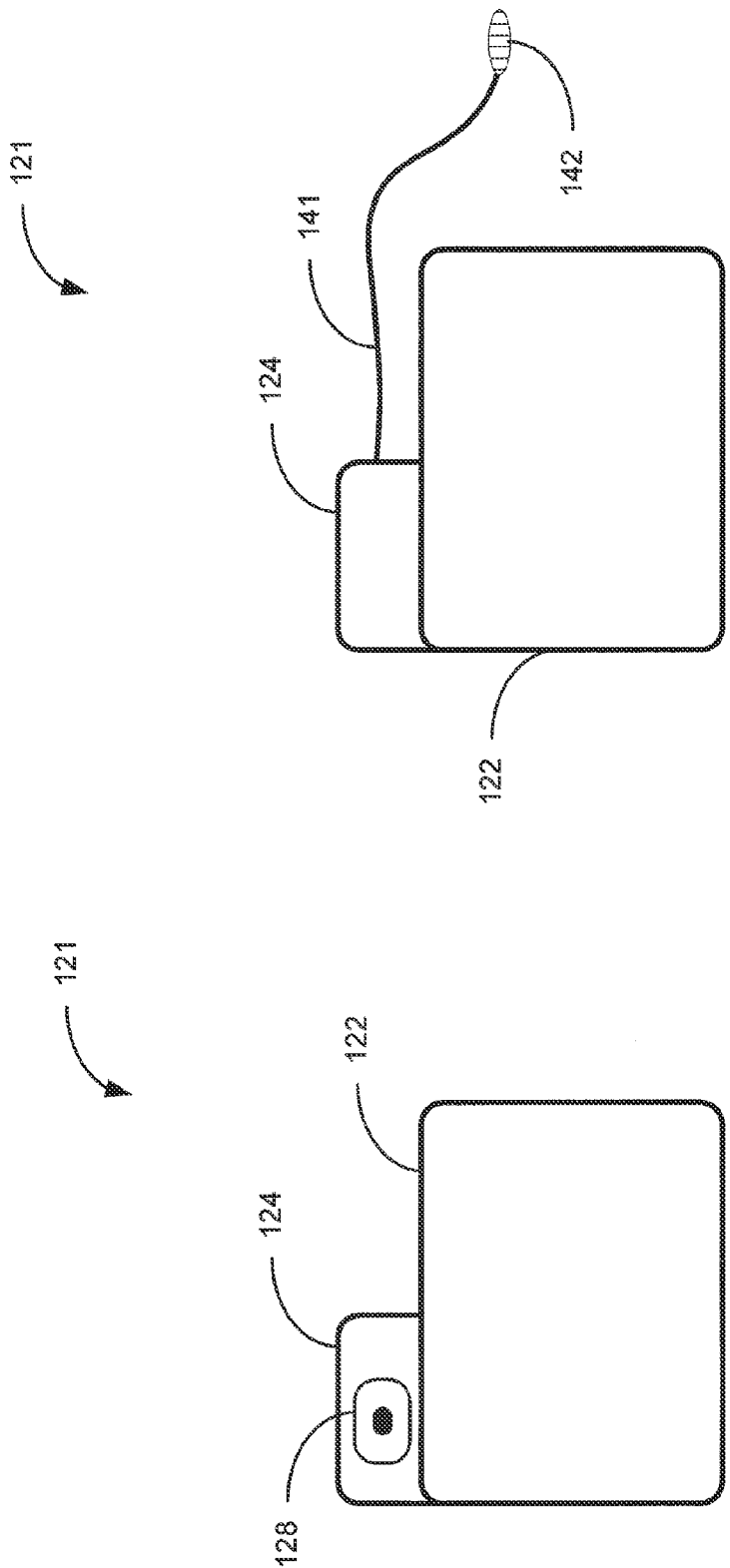

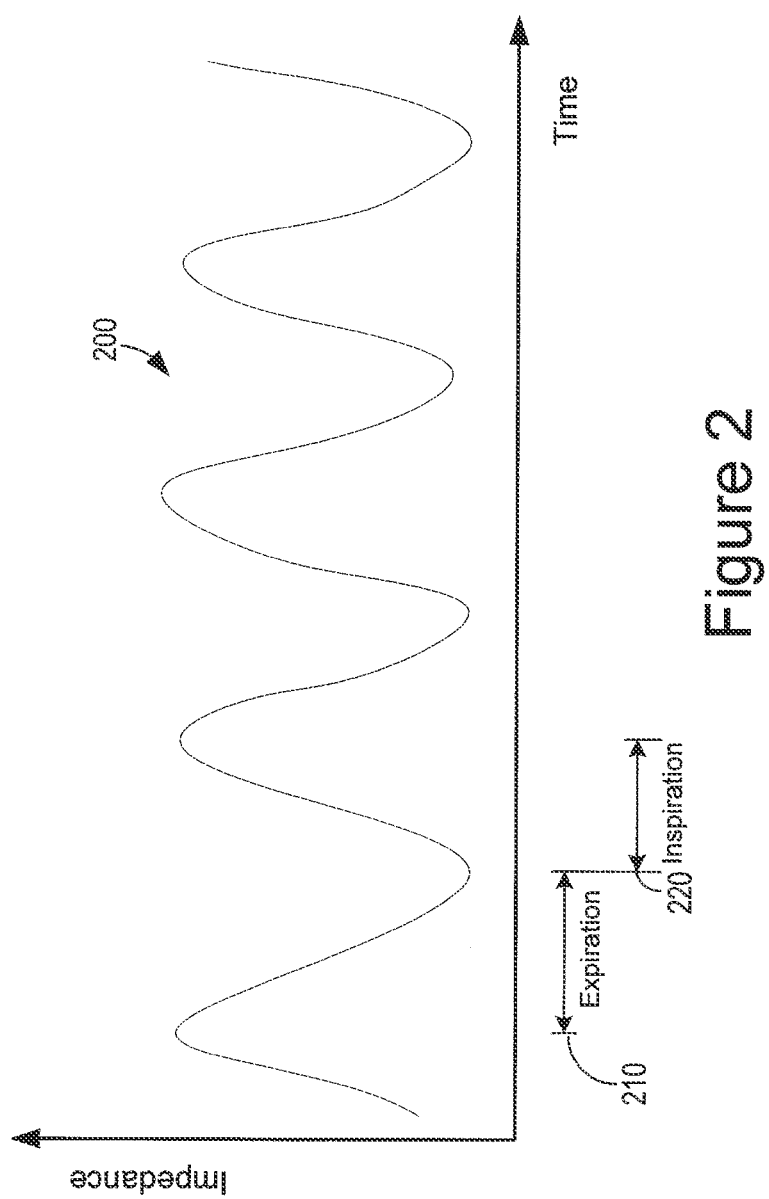

AUTONOMIC AROUSAL DETECTION SYSTEM AND METHOD

RELATED PATENT DOCUMENTS

This application is a continuation of U.S. patent application Ser. No. 10/920,675, filed Aug. 17, 2004, now U.S. Pat. No. 8,606,356, which claims the benefit of Provisional Patent Application Ser. No. 60/504,344, filed on Sep. 18, 2003, to which priority is claimed pursuant to 35 U.S.C. §119(e) and which is hereby incorporated herein by reference.

FIELD OF THE INVENTION

The present invention relates generally to methods and systems for detection of arousals from sleep.

BACKGROUND OF THE INVENTION

Sleep is generally beneficial and restorative to a patient, exerting great influence on the quality of life. The human sleep/wake cycle generally conforms to a circadian rhythm that is regulated by a biological clock. Regular periods of sleep enable the body and mind to rejuvenate and rebuild. The body may perform various tasks during sleep, such as organizing long term memory, integrating new information, and renewing tissue and other body structures.

Lack of sleep and/or decreased sleep quality may be have a number of causal factors including, e.g., nerve or muscle disorders, respiratory disturbances, and emotional conditions, such as depression and anxiety. Chronic, long-term sleep-related disorders e.g., chronic insomnia, sleep-disordered breathing, and sleep movement disorders, including restless leg syndrome (RLS), periodic limb movement disorder (PLMD) and bruxism, may significantly affect a patient's sleep quality and quality of life.

Movement disorders such as restless leg syndrome (RLS), and a related condition, denoted periodic limb movement disorder (PLMD), are emerging as one of the more common sleep disorders, especially among older patients. Restless leg syndrome is a disorder causing unpleasant crawling, prickling, or tingling sensations in the legs and feet and an urge to move them for relief. RLS leads to constant leg movement during the day and insomnia or fragmented sleep at night. Severe RLS is most common in elderly people, although symptoms may develop at any age. In some cases, it may be linked to other conditions such as anemia, pregnancy, or diabetes.

Many RLS patients also have periodic limb movement disorder (PLMD), a disorder that causes repetitive jerking movements of the limbs, especially the legs. These movements occur approximately every 20 to 40 seconds and cause repeated arousals and severely fragmented sleep.

A significant percentage of patients between 30 and 60 years experience some symptoms of disordered breathing, primarily during periods of sleep. Sleep disordered breathing is associated with excessive daytime sleepiness, systemic hypertension, increased risk of stroke, angina and myocardial infarction. Disturbed respiration can be particularly serious for patients concurrently suffering from cardiovascular deficiencies. Disordered breathing is particularly prevalent among congestive heart failure patients, and may contribute to the progression of heart failure.

Sleep apnea is a fairly common breathing disorder characterized by periods of interrupted breathing experienced during sleep. Sleep apnea is typically classified based on its etiology. One type of sleep apnea, denoted obstructive sleep apnea, occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and occasionally for a minute or longer.

In addition to apnea, other types of disordered respiration have been identified, including, for example, hypopnea (shallow breathing), dyspnea (labored breathing), hyperpnea (deep breathing), and tachypnea (rapid breathing). Combinations of the disordered respiratory events described above have also been observed. For example, Cheyne-Stokes respiration (CSR) is associated with rhythmic increases and decreases in tidal volume caused by alternating periods of hyperpnea followed by apnea and/or hypopnea. The breathing interruptions of CSR may be associated with central apnea, or may be obstructive in nature. CSR is frequently observed in patients with congestive heart failure (CHF) and is associated with an increased risk of accelerated CHF progression.

An adequate duration and quality of sleep is required to maintain physiological homeostasis. Untreated, sleep disturbances may have a number of adverse health and quality of life consequences ranging from high blood pressure and other cardiovascular disorders to cognitive impairment, headaches, degradation of social and work-related activities, and increased risk of automobile and other accidents.

SUMMARY OF THE INVENTION

The present invention is directed to systems and methods for detecting arousals of a patient during sleep. One embodiment of the invention is directed to a method for acquiring sleep information including autonomic arousal events. The method involves sensing one or more physiological conditions modulated by a patient's autonomic arousal response. Autonomic arousal events occurring during sleep are detected based on the one or more sensed signals. At least one of sensing the physiological signals and detecting the autonomic arousal events is performed at least in part implantably.

Another embodiment of the invention is directed to a method for acquiring sleep-related information. An arousal signal modulated by changes in muscle tone associated with autonomic arousal is sensed using a sensor disposed on an implantable therapy device. Autonomic arousal events are detected based on the arousal signal.

Yet a further embodiment of the invention involves a method for detecting arousals from sleep. One or both of a signal modulated by brainwave activity associated with an autonomic arousal response and a signal modulated by changes in muscle tone associated with the autonomic arousal response are generated. Autonomic arousal events are detected, using an implantable device, based on at least one of the brainwave signal and the muscle tone signal.

Another embodiment of the invention involves a system for detecting autonomic arousal events. The system includes an implantable therapy device and one or more sensors mechanically coupled to the implantable therapy device. The sensors are configured to sense one or more physiological conditions modulated by a patient's autonomic arousal response. An arousal detector is coupled to the sensor and is configured to detect autonomic arousal events based on the sensed physiological conditions.

In accordance with another embodiment of the invention, a system detects autonomic arousal events occurring during sleep. The system includes one or more sensors configured to sense one or more physiological conditions associated with a patient's autonomic arousal response. An implantable arousal detector is coupled to the one or more sensors. The arousal detector is configured to detect autonomic arousal events based on the one or more physiological conditions.

One embodiment of the invention is directed to a medical system detecting autonomic arousal events occurring during sleep. The system includes one or more sensors configured to sense one or more physiological conditions associated with a patient's autonomic arousal response. The system also includes an implantable arousal detector coupled to the one or more sensors. The arousal detector is configured to detect autonomic arousal events based on the one or more physiological conditions.

BRIEF DESCRIPTION OF THE DRAWINGS

FIGS. 1F-1I are diagrams illustrating various configurations of an arousal sensor coupled to an implanted medical device in accordance with embodiments of the present invention;

FIG. 2 is a graph of a normal respiration signal measured by a transthoracic impedance sensor that may be utilized in accordance with embodiments of the present invention;

Figure 1A:
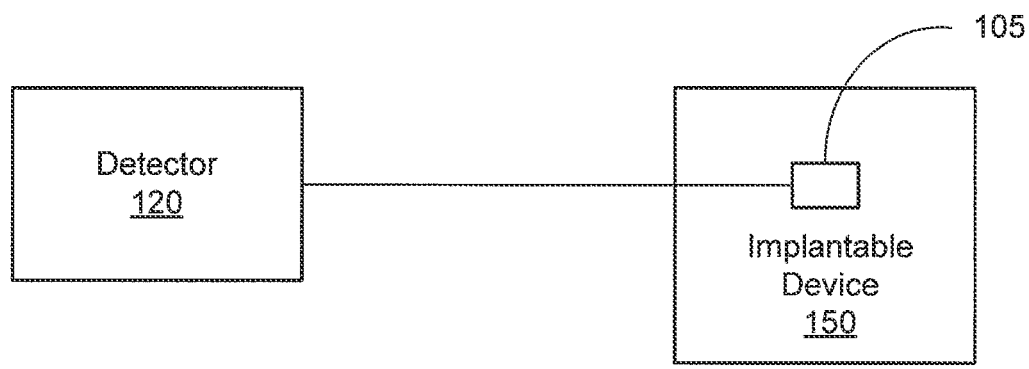
FIGS. 1A-1D are a block diagrams of systems that may be used to implement arousal detection in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the present invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

An adequate quality and quantity of sleep is required to maintain physiological homeostasis. Prolonged sleep deprivation or periods of highly fragmented sleep ultimately will have serious health consequences. Chronic fragmented sleep may be associated with various cardiac or respiratory disorders affecting a patient's health and quality of life.

Assessment of sleep is traditionally performed in a polysomnographic sleep study at a dedicated sleep facility. Polysomnographic studies involve acquiring sleep-related data, including the patient's typical sleep patterns and the physiological, environmental, contextual, emotional, and other conditions affecting the patient during sleep. However, such studies are costly, inconvenient to the patient, and may not accurately represent the patient's typical sleep behavior. Sleep assessment in a laboratory setting presents a number of obstacles in acquiring an accurate picture of a patient's typical sleep patterns including arousals and sleep disorders. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Various aspects of sleep quality, including number and severity of arousals, number and severity of autonomic arousal events, sleep disordered breathing episodes, nocturnal limb movements, and cardiac, respiratory, muscle, and nervous system functioning may provide important information for diagnosis and/or therapy delivery. Superficially, sleep may viewed as a monolithic event that is characterized by a period of unconsciousness. If examined in greater detail, sleep periods may be described as involving a series of events or stages. For example, sleep is typically divided into various stages of sleep, including rapid eye movement (REM) sleep and non-REM (NREM) sleep. Non-REM sleep may be further subdivided into stage 1, stage 2 and stage 3 non-REM sleep, for example.

One indicator of sleep quality is the number of arousals experienced during sleep. An arousal is an event that occurs during sleep and may be identified based on changes in electroencephalogram (EEG) signals during non-REM sleep and changes in EEG and electromyogram (EMG) signals during REM sleep. Arousal events may or may not culminate in wakefulness. The patient may experience an arousal event during sleep and never wake up.

In one implementation, arousal from sleep has been identified, for example, based on a shift in the patient's EEG signal to a higher frequency for a specified period of time during non-REM sleep assuming sleep has been previously detected. Arousals during REM sleep have been identified by the EEG arousal defined above in addition to changes in an EMG signal or body movements. Arousals, as identified based on changes in EEG signals, encompass activation of the patient's autonomic nervous system.

Activation of the patient's autonomic nervous system during sleep may be used to identify arousal events referred to herein as an autonomic arousal event. Autonomic arousal events may be identified by an autonomic arousal response involving transient activation of the patient's autonomic nervous system. The autonomic arousal response may or may not result in detectable changes to the patient's EEG signal.

Autonomic arousal events comprise transient changes during sleep that affect autonomic physiological parameters such as heart rate, blood pressure, cardiac output, peripheral vasoconstriction, sympathetic nerve traffic, and arteriole size, among other conditions. For example, an autonomic arousal event may be detected based on a change of about 4 mm Hg increase in systolic blood pressure and/or about a 4 beat per minute increase in heart rate. As previously mentioned, autonomic arousal events begin during sleep and may or may not result in wakefulness. Thus, the patient may experience a number of autonomic arousal events while asleep without achieving a waking state. Nevertheless, these autonomic arousal events disrupt the patient's sleep and degrade sleep quality.

Information about the autonomic arousal events may be stored in memory, and/or transmitted to a separate device for printing or display. Information about the autonomic arousal events may be used to diagnose sleep disorders and/or adjust patient therapy, such as cardiac stimulation therapy, drug therapy, neural stimulation therapy, and/or respiration therapy. Trending sleep information including autonomic arousal events and correlating the sleep information with sleep disorder events may be helpful in determining and maintaining appropriate therapies for patients suffering from a range of sleep disorders.

Many sleep disorder events, e.g., disordered breathing events and movement disorder events, are followed by autonomic arousal events. These autonomic arousals disrupt the normal sleep pattern and may be involved in causing chronic hypertension. The autonomic arousal response may be visible on signals generated by electroencephalogram (EEG) sensors, electromyogram (EMG) sensors, and/or other sensors sensitive to autonomic nervous system changes.

In accordance with embodiments of the present invention, information related to the patient's autonomic arousal response may be collected and/or analyzed. The identification of autonomic arousal events may be used for a variety of purposes, including detecting and/or verifying sleep disorder events, trending the number of arousals per night, and developing various indices such as an arousal index and/or a composite index based on arousals and sleep disorder events. The arousal information may be collected and used in the evaluation of sleep and/or sleep disorders.

Frequent arousals are indicative of a number of medical disorders, including sleep disorder such as nocturnal periodic limb movement syndrome and/or sleep disordered breathing. Further, frequent arousals of the sympathetic nervous system may lead to chronic hypertension or other medical problems. The ability to detect individual and/or aggregate arousals may be used in diagnosing various medical disorders, including disordered breathing, movement disorders, and hypertension, for example.

If the patient receives therapy to treat a diagnosed medical disorder, then the ability to count and trend arousals also provides information regarding therapy efficacy. For example, if arousals decline after therapy is delivered, then it may be assumed that the therapy provides an effective treatment for the diagnosed medical disorder. Further, detection of an arousal following delivery of therapy may be used to provide feedback for therapy control.

The methodologies described herein involve using arousal information in combination with disordered breathing information. For example, the system may provide the capability of discriminating between disordered breathing events that cause arousals and disordered breathing events that do not cause arousals. The detection of arousals may allow trending of arousals that occur during sleep. The disordered breathing events that are followed by arousals are considered to be the most disruptive, because repeated arousals prevent the patient from receiving a restful sleep. Some patients continue to experience disordered breathing events during an aroused status. It may be desirable to ignore disordered breathing events that occur during an aroused state. The ability to detect an arousal and ignore subsequently detected disordered breathing events during arousal may improve the accuracy of disordered breathing indices, e.g., apnea/hypopnea index.

Figure 1B:
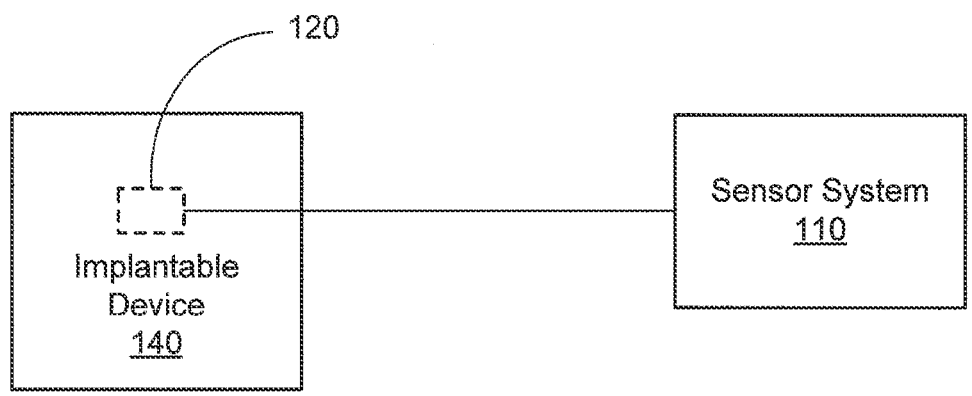
Figure 1C:
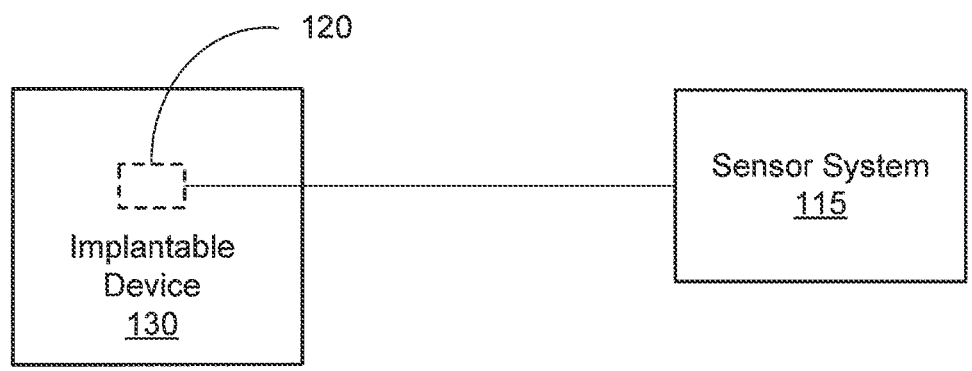

FIGS. 1A through 1C illustrate embodiments of the invention directed to detection arousal from sleep. As depicted in FIG. 1A, an arousal detection system may comprise, for example, a sensor 105 that generates a signal modulated by changes in muscle tone associated with autonomic arousal. Such a signal may be generated, for example, using an electromyogram sensor or a strain gauge positioned in contact with or near skeletal muscle, such as the pectoral muscle. The sensor 105 is disposed on an implantable device 150, such as an implantable cardiac rhythm management system (pacemaker, defibrillator, cardiac monitor, cardiac resynchronizer), implantable drug pump, implantable neural stimulator, or other implantable diagnostic or therapeutic device. The implantable device 150 may implantably monitor various physiological conditions and deliver therapy to the patient. For example, the implantable device may deliver cardiac stimulation therapy, neural stimulation therapy, drug therapy, and/or other therapies or combinations of therapies to treat various diseases or disorders affecting the patient. In some embodiments, the implantable device delivers therapy to treat sleep disorders, for example. Implantably performing an operation comprises performing the operation using a component, device, or system that is partially or fully implanted within the body.

The sensor 105 may be positioned on the housing, header, lead system, or other component of the implantable device 150 so that the sensor 105 is in contact with, or near, skeletal muscle. The sensor 105 generates signals modulated by changes in muscle tone associated with autonomic arousal from sleep. The sensor 105 is communicatively coupled to an arousal detector 120. The sensor 105 and the arousal detector 120 may communicate through a wired or wireless communication link, for example. The arousal detector 120 detects arousals from sleep based on the signal generated by the sensor 105.

FIG. 1B illustrates another embodiment of the invention. A sensor system 110 may comprise one or both of a muscle tone sensor e.g., an EMG sensor, configured to generate a signal modulated with changes in muscle tone associated with autonomic arousals and a brainwave sensor, e.g., an EEG sensor, configured to generate a signal modulated by brainwave activity associated with autonomic arousals. The EMG sensor generates signals modulated by changes in muscle tone associated with autonomic arousals from sleep. The EEG sensor generates a signal modulated by brainwave activity associated with autonomic arousals from sleep. The EMG and EEG sensors are communicatively coupled to an arousal detector 120 disposed within a housing of an implantable device 140. The arousal detector 120 detects arousals from sleep based on at least one of the EEG signal and the EMG signal.

Other sensors may be used in connection with arousal detection. For example, an accelerometer may be employed to detect patient movement correlated to arousal. An electrogram or other cardiac sensor may be used to detect various cardiac parameters associated with arousal. For example, heart rate increases upon arousal, the AV delay decreases upon arousal, and heart rate variability is modified by autonomic tone changes associated with arousal. Cardiac output increases during arousal, as may be measured via an impedance sensor. Blood pressure, measured, for example, by a lead-based pressure gauge, is modulated by arousal and may be utilized in arousal detection. Peripheral arterial tonography may be used in arousal detection. Arteriole size, which may be measured by photoplethysmography, decreases upon arousal due to sympathetic nervous system activation. Sympathetic nerve traffic modulated by arousal may be sensed using microelectrodes coupled to an implantable device.

The implantable device 150 may monitor various physiological conditions and/or deliver therapy to the patient. For example, the implantable device may deliver cardiac stimulation therapy, neural stimulation therapy, drug therapy, or other therapies or combinations of therapies to treat diseases or disorders affecting the patient. The implantable device may deliver therapy to treat sleep disorders, for example.

The block diagram of FIG. 1C depicts another embodiment of a system that may be used to detect arousals from sleep. The system includes a detector 115 configured to detect changes in the patient's nervous system. The changes may comprise sympathetic and/or parasympathetic nervous system changes. The system also includes an arousal detector in an implantable device, the arousal detector configured to detect arousals from sleep based on the nervous system changes. The system may be configured to detect the presence of individual arousal events, the presence of aggregate arousals, or the presence of both individual and aggregate arousals.

For example, in one implementation, the sensors may sense conditions that are modulated contemporaneously with an arousal event. In this implementation, the system may detect an individual arousal event during or slightly after the occurrence of the arousal event, for example. In another implementation, the sensors may be sensitive to conditions that are modulated by the aggregate effect of multiple arousal events that occur over a period of time. In such an implementation, detection of individual arousals may or may not occur. The implantable device 130 may detect changes in physiological conditions that are caused by the occurrence of multiple arousals. The changes in the physiological conditions are used by the system to determine that multiple arousal events that have occurred over a period of time. A representative set of conditions indicative of the occurrence of multiple arousal events over a period of time may include, heart rate variability, blood pressure, AV-delay, arteriole size, sympathetic nerve activity, among others. This list is not exhaustive and other conditions may be sensed by the system to determine the occurrence of multiple arousal events.

Figure 1D:
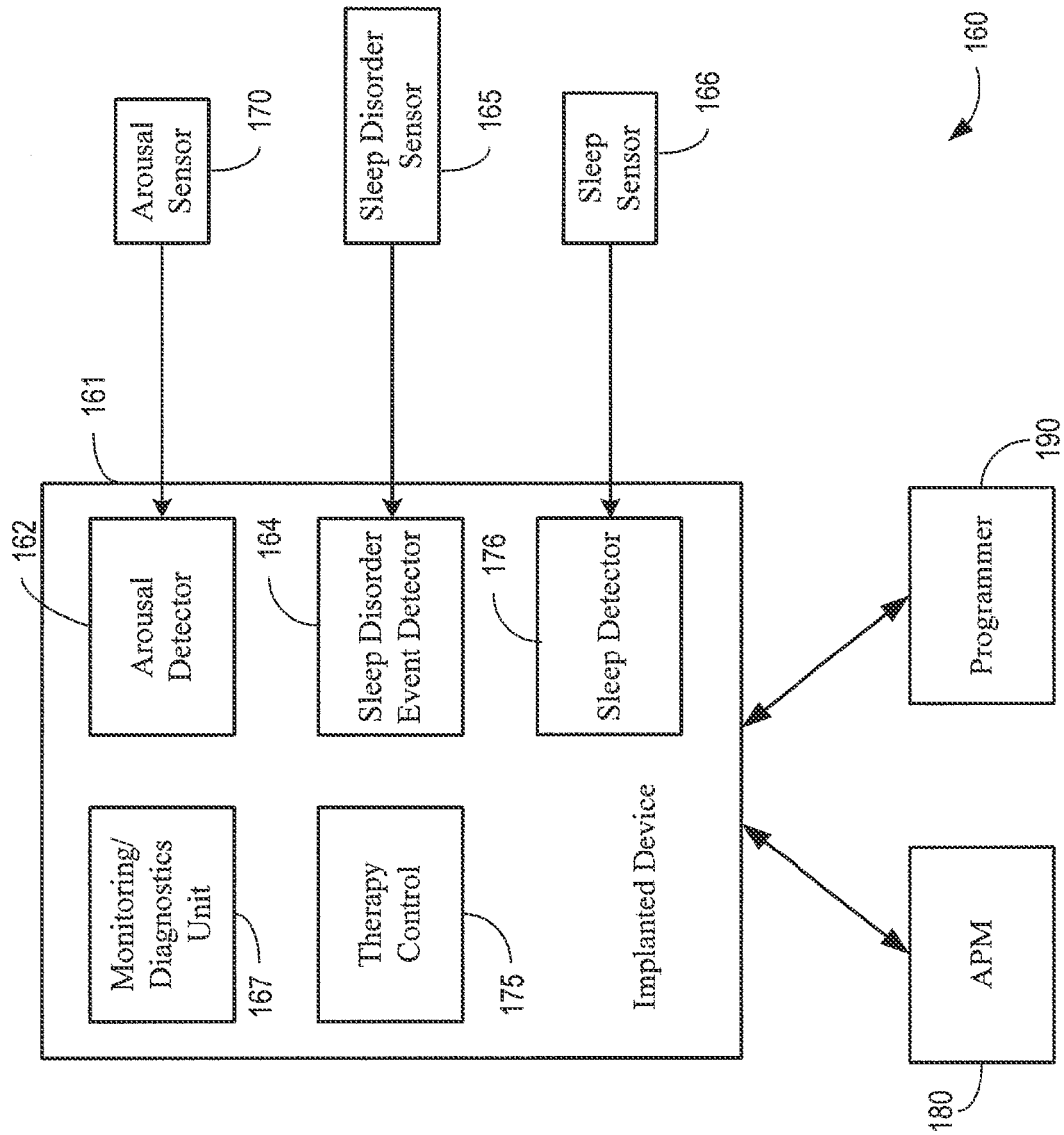

FIG. 1D illustrates an embodiment of the present invention involving detection of arousals during sleep periods. The processes and systems exemplified by these embodiments may be implemented alone or in combination with one or more processes and systems exemplified by other embodiments described herein to provide a coordinated approach to patient monitoring, diagnosis, and/or therapy.

As is illustrated in FIG. 1D, a system 160, in accordance with an embodiment of the present invention, may include one or more patient-internal and/or patient-external sensors 170 for sensing the autonomic arousal response of the patient. In one configuration, one or more EMG sensors may be used. In other configurations, one or more EEG sensors, a combination of one or more EMG sensors and one or more EEG sensors, and/or one or more other types of sensors capable of sensing arousal may be employed.

If EMG sensors are employed, the sensors are positioned on or near muscles and used to sense muscle electrical signals (myopotentials) associated with the autonomic arousal response. In one example, the EMG sensors are placed on the header, housing, or lead system of an implanted device. For example, the EMG sensors may be placed on the housing of a cardiac device capable that is capable of sensing cardiac activity and/or delivering electrical stimulation to the heart. The cardiac device housing may be implanted in the pectoral region. In this implementation, the EMG sensors are positioned to detect arousals based on the electrical activity of the pectoral muscle.

Alternatively, or additionally, the system 160 may include, for example, one or more EEG sensors used to detect brain activity. The EEG sensors may be positioned on a respiratory mask assembly such as on the respiratory mask and/or respiratory mask strap of a CPAP device, for example, or may be positioned appropriately to detect brain activity. Signals from the one or more sensors 170 may be transmitted to an arousal detector 162 located in an implantable device 161 via leads or a wireless communication link, for example.

The implanted medical device 161 may perform one or a combination of monitoring, diagnostic, and/or therapeutic functions. Arousal information may be stored in the memory of a monitoring/diagnostic unit 167 of the implanted medical device 161. The monitoring/diagnostic unit 167 may include a processor for making evaluating the arousal information and/or determining values or indices using the arousal information. For example, the monitoring/diagnostic unit processor may determine the number of arousals occurring within a sleep period, or other specified time period. The monitoring/diagnostic unit processor may determine an arousal index (arousals detected per unit time), an apnea/hypopnea index (apneas or hypopneas detected per unit time), or other indices.

Further, the monitoring/diagnostic unit processor may evaluate the sleep disorder events to determine if arousals are associated with the sleep disorder events. For example, if an arousal is detected within a predetermined time period after a sleep disorder event is detected, the arousal may be associated with the sleep disorder event. Using this process, arousals from sleep that are associated with sleep disorder events can be discriminated from arousals from sleep that are not associated with sleep disorder events.

The arousal information may be processed, trended, displayed, and/or transmitted to another device, such as an advanced patient management (APM) system 180 or a programmer 190, periodically or on command. Advanced patient management systems involve a system of medical devices that are accessible through various communications technologies, including wireless and wired communication links. Patient data may be downloaded from one or more of the medical devices periodically or on command, and stored at the patient information server. The physician and/or the patient may communicate with the medical devices and the patient information server, for example, to provide or acquire patient data or to initiate, terminate or modify therapy.

The data stored on the patient information server may be accessible by the patient and the patient's physician through one or more terminals, e.g., remote computers located in the patient's home or the physician's office. The patient information server may be used to communicate to one or more of the patient-internal and patient-external medical devices to provide remote control of the monitoring, diagnosis, and/or therapy functions of the medical devices.

In one embodiment, the patient's physician may access and evaluate patient data transmitted from the medical devices to the patient information server. After evaluation of the patient data, the patient's physician may communicate with one or more of the patient-internal or patient-external devices through the APM system to initiate, terminate, or modify the monitoring, diagnostic, and/or therapy functions of the patient-internal and/or patient-external medical systems. Systems and methods involving advanced patient management techniques are further described in U.S. Pat. Nos. 6,336,903, 6,312,378, 6,270,457, and 6,398,728, hereby incorporated herein by reference.

In one application, for example, the number of arousals may be counted and used to calculate an arousal index to quantify the number of arousals experienced by the patient per unit time. Arousal information may be used to determine a number of sleep quality indices. Various approaches for sleep quality assessment that may be utilized in connection with embodiments of the invention, such as the implementation of various sleep quality indices, are described in commonly owned U.S. patent application Ser. No. 10/642,998, filed Aug. 18, 2003, now U.S. Pat. No. 8,002,553, and incorporated herein by reference.

Autonomic arousal represents a sleep stage that may be detected by the approaches described herein. Arousal detection may be utilized in connection with determining sleep stage and information about various sleep stages experienced by the patient. Various processes for acquiring information about sleep stages, some of which may be used in connection with embodiments described herein, are described in commonly owned U.S. patent application Ser. No. 10/643,006, filed Aug. 18, 2003, now U.S. Pat. No. 8,192,376, and incorporated herein by reference.

The arousal information may be used in diagnosing and treating a variety of disorders, including nocturnal sleep disorders, such as periodic leg movement disorder, sleep disordered breathing, such as sleep apnea, hypertension, and other conditions. The ability to count and trend these arousals provides diagnostic information regarding patient status with respect to the disorders. For example, autonomic arousals are associated with causing hypertension. A presence of hypertension may be determined or predicted based on arousal information, such as a trend of arousal events over time. Trending arousals may be used to improve therapy used to treat sleep disorders.

Arousals fracture sleep staging, leading to disrupted sleep, and as a consequence, daytime sleepiness. An arousal will bring a patient out of REM sleep or deep sleep (stage 3-4), and bring them temporarily to a waking state. As a consequence, the amount of REM and deep sleep is limited, since the patient has to go back through Stage 1-2 sleep before they enter REM or deep sleep.

The implanted device 161 may include a sleep detector 176 and one or more sleep sensors 166 for determining the onset and/or offset of sleep. The sleep detector 176 may determine the sleep state of the patient using one or more patient conditions related to sleep, such as activity level, time of day, heart rate, respiration rate, posture, proximity to bed, and/or other factors indicative of sleep. Sleep detection may involve, for example, sensing sleep-related conditions and comparing the sensed sleep-related conditions to thresholds. The patient's sleep state may be determined based on the comparison. In one embodiment described below, sleep detection involves comparing a first sleep-related parameter to a threshold that is modulated by a second sleep-related parameter. Automatic sleep detection facilitates calculation of various indices used to assess sleep quality such as number of arousals per sleep period, and/or other indices based on sleep period, for example.

In one configuration, arousal information may be used by a therapy control unit 175 within the implantable device 161 for initiating, terminating, or adjusting therapy. Alternatively, the arousal information may be transmitted to the APM system 180 or other remote device for automatic or physician conducted analysis. The APM system 180 may transmit control signals to the implanted device 161 to initiate, terminate or modify therapy delivered by the implanted device 161. For example, arousal feedback information may be used by an APM system, an implantable cardiac device, an external respiration therapy device, or other therapy device or combinations of devices to provide closed-loop control of the therapy using arousal information feedback.

In one configuration, the arousal detector 162 is a component of the implanted device 161 and is positioned within the implanted device housing, for example. The arousal detection function may alternatively be performed in a patient-internal or patient-external device other than the implanted device 161, such as an APM system 180, for example. In this configuration, sensor data collected by the implanted device 161 from the sensors 170 may be transmitted to the APM system 180 and used for arousal detection.

Detection of arousals involves evaluating the arousal information acquired from the sensors 170 for a characteristic signature of autonomic arousal. Autonomic arousal responses, as detected using EEG sensors and EMG sensors, are illustrated in the graph of FIG. 1B.

Figure 1E:
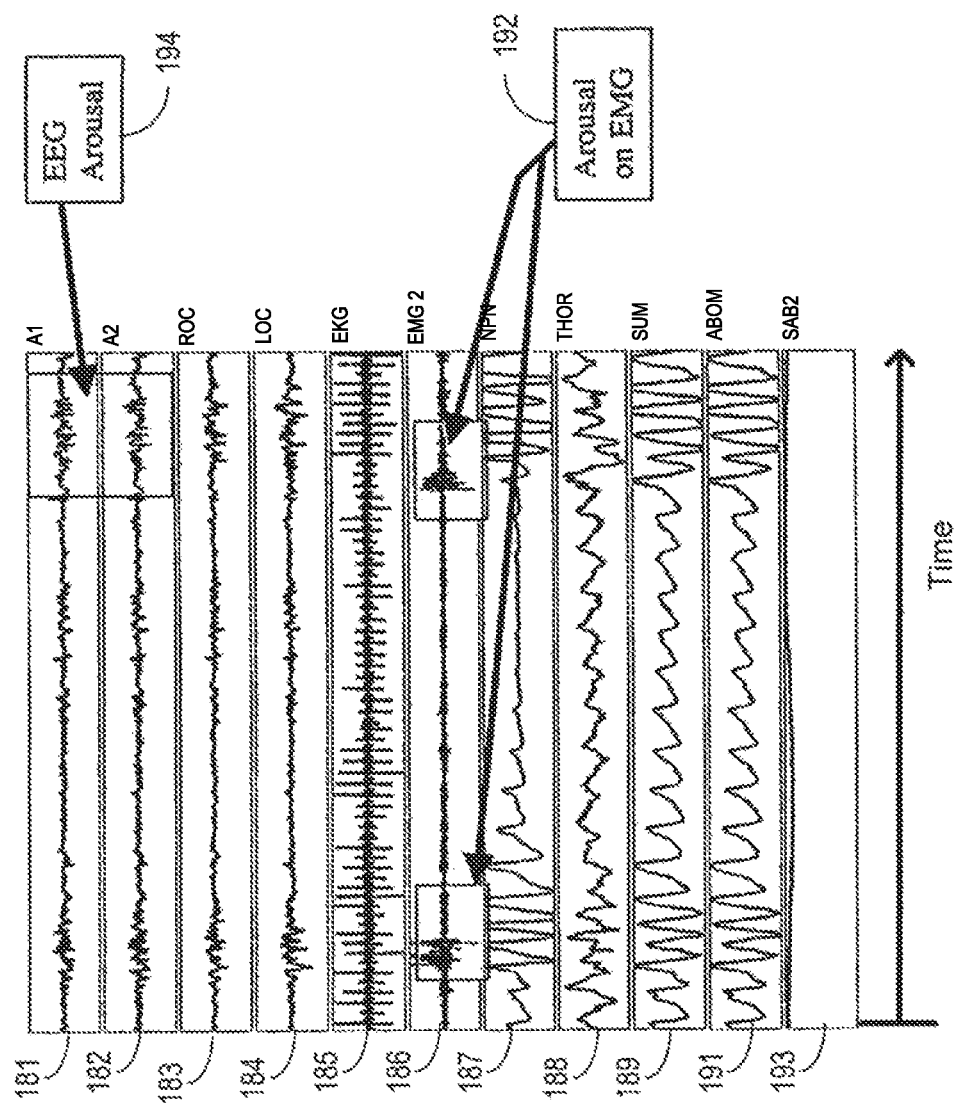
FIG. 1E illustrates graphs of signals from an electroencephalogram (EEG) sensor and an electromyogram (EMG) sensor used for arousal detection in accordance with embodiments of the present invention.
Figure 1G:
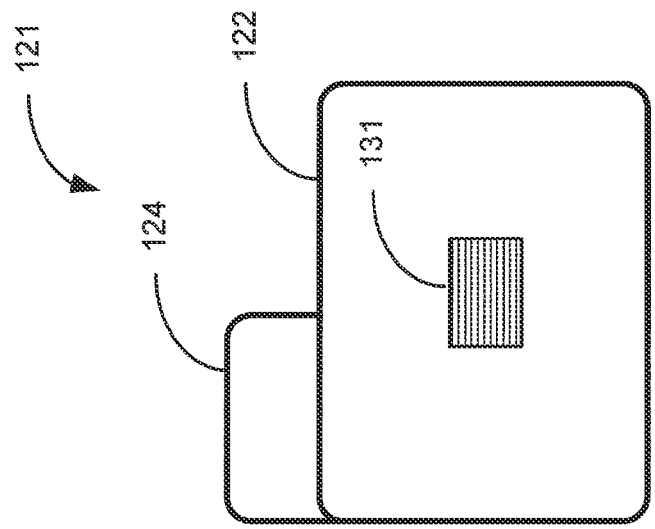

Referring now to FIG. 1E, a sleep study sensor array output is illustrated including an apnea event terminating in an arousal. Arousal detection may be implemented using implantable sensors capable of detecting changes in the sympathetic or parasympathetic nervous system. These changes may be either short-term (i.e., changes associated with individual arousals) or long-term (i.e., aggregate effect of multiple arousals). A short-term effect of arousal includes, for example, the activation of sympathetic nerve activities. Sympathetic or parasympathetic changes, or the changes of autonomic balance can be assessed, for example, by heart rate variability (HRV), which can be detected using a device configured to sense cardiac activity, changes in heart rate, and/or changes in AV conduction.

In the graphs of FIG. 1E, the abscissa of all the graphs is the same time period during the sleep analysis of a patient. The ordinate of each of the graphs is the signal amplitude of the respective sensor. Traces 181, 182, 183, and 184 are the top, second, third, and fourth traces respectively, plotted from sensors adapted to produce electroencephalogram (EEG) signals. Evident in all four traces, but particularly pointed out in traces 181 and 182 is a characteristic signature of an EEG signal indicative of arousal 194. A trace 185 provides an electrocardiogram (EKG) of the heart beats during the time period of the graph. A trace 186 provides an electromyogram defining muscular movement during the time period of the graph. Particularly evident in the trace 186 is a characteristic signature of an EMG signal indicative of arousal 192.

Traces 187, 188, 191, and 189 illustrate various parameters related to respiration. Trace 187 is nasal pressure, 188 is thoracic effort, 191 is abdominal effort, and 189 is the sum of the thoracic and abdominal effort. Trace 193 depicts the blood oxygen saturation level of the patient. Pulmonary activity may be sensed through the use of internal sensors, such as impedance sensors and/or minute ventilation sensors described further below.

In accordance with aspects of the present invention, arousal detection may be used in connection with detection of sleep disorders, such as disordered breathing. Sleep disorders, such as disordered breathing and/or PLMD may cause the patient to arouse from sleep frequently during a sleep period. Thus arousals from sleep follow the sleep disorder event. In one configuration, arousal detection may be used as a surrogate for direct detection of the disordered condition. For example, in systems that do not have a respiration sensor capable of detecting disrupted respiration, arousal detection may be used as a surrogate for detecting disrupted respiration. In systems that do not have a sensor capable of detecting nocturnal limb movements, arousal detection may be used as a surrogate for detecting PLMD, or other movement disorders.

In one implementation, arousal detection may be combined with sleep disorder event detection to verify the occurrences of sleep disorders. Referring again to FIG. 1D, the system 160 may include sleep disorder event detector 6015 for sensing patient conditions associated with sleep disorders, e.g., sleep apnea and PLMD. In one configuration, the sleep disorder sensor system 6015 includes a transthoracic impedance sensor capable of sensing respiration. The respiration signals are evaluated by a sleep disorder event detector 164 to detect occurrences of disordered breathing. In another configuration, the sleep disorder sensor system 6015 includes an accelerometer positioned on a limb of the patient to sense nocturnal movements. The accelerometer signals are evaluated by the sleep disorder event detector 164 to detect occurrences of sleep movement disorders.

Arousal information may be used by the sleep disorder event detector 164 to augment detection of sleep disorder events. For example, arousal information may be used to confirm occurrences of disordered breathing as described earlier. Arousal information may be used to distinguish between correctly and incorrectly identified sleep disorder events indicated by the sleep disorder event detector 164.

Further, information from the arousal detector may be used to separate sleep disorder events, e.g., apnea, hypopnea and/or PLMD, followed by arousal versus those terminated without arousal. The sleep disorder events that are followed by arousal are considered to be the most disruptive, as these arousals interrupt the normal course of sleep and prevent the patient from receiving a full sleep cycle each night. Detecting these types of sleep disorder events enhances the specificity of sleep disorder event detection and guides diagnosis and/or therapy.

The arousal information may be used to modify therapy for sleep disorder events such as disordered breathing. In various implementations, the arousal information and/or disordered breathing information may be used by a therapy control unit 175 in the implanted device 161 to modify disordered breathing therapy delivered to the patient. The therapy may be delivered by the implanted device, or by a separate, possibly external, therapy device.

For example, electrical stimulation therapy may be provided by the implanted device 161. Detection of disordered breathing may be used to initiate the electrical stimulation therapy. Detection of arousal, indicating the end of the disordered breathing event, may be used to terminate the electrical stimulation therapy, for example.

In another example, electrical stimulation therapy may be provided, and the number of arousals monitored. If the electrical stimulation therapy causes too many arousals, the electrical stimulation therapy may be adjusted or terminated.

In another example, the APM system 180 may receive information about sleep disorder events from the sleep disorder event detector 164 and/or arousal information from the arousal detector 162. The information may be automatically evaluated by the APM system 180, or may be evaluated by the patient's physician. The APM system 180 may be used to transmit control signals to the therapy control unit 175 of the implanted device 161 to initiate, terminate or modify the therapy delivered to the patient.

In various configurations, an EMG sensor may be positioned on a housing or header of an implantable device, such as a cardiac rhythm management device, or may be located on a catheter or lead coupled to the cardiac rhythm management device. An EMG sensor located on a device positioned in the pectoral region provides access to skeletal muscle that may be exploited to detect arousal.

FIGS. 1F-1I illustrate various configurations of an arousal sensor mechanically coupled to an implanted medical device 121, such as an implantable pacemaker or implantable cardioverter/defibrillator in accordance with embodiments of the invention. The implantable medical device 121 may include a housing 122 enclosing the medical device circuitry and a header 124 for coupling a lead system 141 to the circuitry of the medical device 121.

Figure 1F:
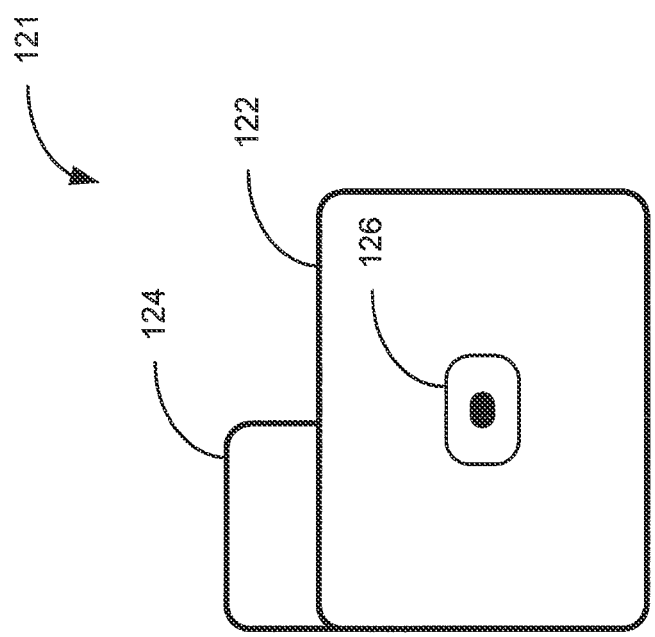

An arousal sensor may be implemented, for example, using an electromyogram (EMG) electrode 126 or force responsive sensor 131 positioned on the housing 122 of the medical device 121 as illustrated in FIGS. 1C and 1D, respectively. FIG. 1H illustrates an arousal sensor 128 positioned on the header 124 of the medical device 121. Alternatively, an arousal sensor 142, e.g., EMG electrode or strain gauge, may be positioned on the lead system 141 or may be coupled to the housing 122 through a catheter or lead system 141, such as by using the header 124, as illustrated in FIG. 1F.

Figure 3A:
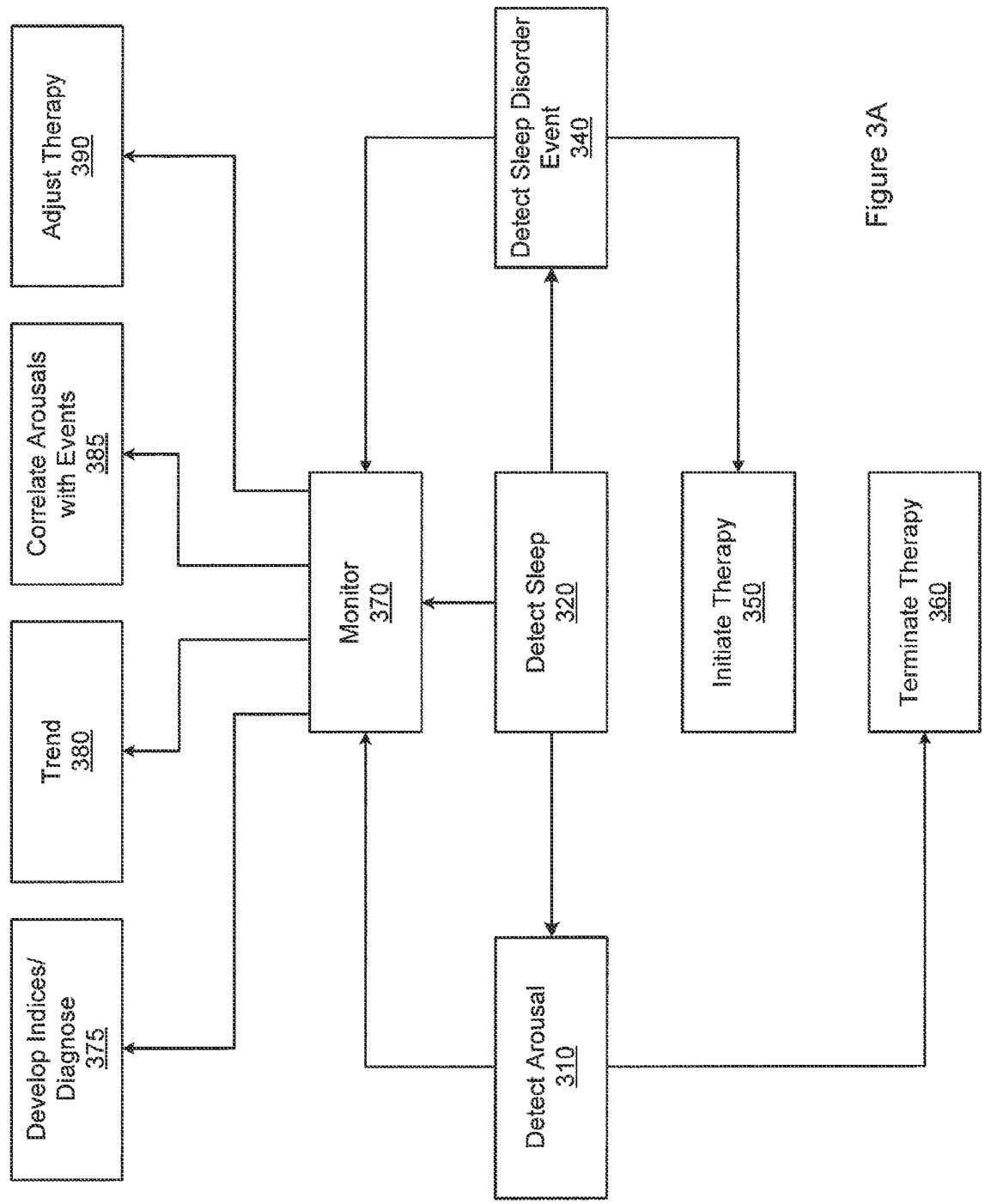
FIG. 3A depicts a flow diagram illustrating various optional processes that may be implemented in connection with arousal detection according to embodiments of the invention.

FIG. 3A depicts a flow diagram illustrating various optional processes that may be implemented in connection with arousal detection according to embodiments of the invention. Detection of sleep 320 may be used to inform the arousal detection process 310 and the sleep disorder event detection process 340. Information about sleep, sleep disorder events, and arousals from sleep are monitored 370. The information may be used to diagnose sleep-related disorders and/or other disorders 375, calculate arousal and sleep disorder indices, develop trend information 380, correlate arousals with sleep disorder events 385, and/or adjust therapy delivered to the patient 390. Upon detection of a sleep disorder event 340, e.g., sleep disordered breathing, therapy to mitigate the sleep disorder event may be initiated 350. Arousal detection 310 signals the end of the sleep disorder event, and therapy may be terminated 360 following detection of arousal from sleep.

Various embodiments of the invention involve the use of arousal detection cooperation with sleep detection. Various aspects of sleep quality, including number and severity of arousals, sleep disordered breathing episodes, nocturnal limb movements, correlation of sleep disorder events to arousals, and other cardiac, respiratory, muscle, and nervous system functioning may provide important information for diagnosis and/or therapy delivery. An initial step to sleep quality evaluation is an accurate and reliable method for discriminating between periods of sleep and periods of wakefulness. Various approaches to sleep detection, some of which may be used in combination with embodiments of the invention presented herein, are described in commonly owned U.S. patent application Ser. No. 10/309,771, now U.S. Pat. No. 7,189,204, filed Dec. 4, 2002, and incorporated herein by reference.

Figure 3B:
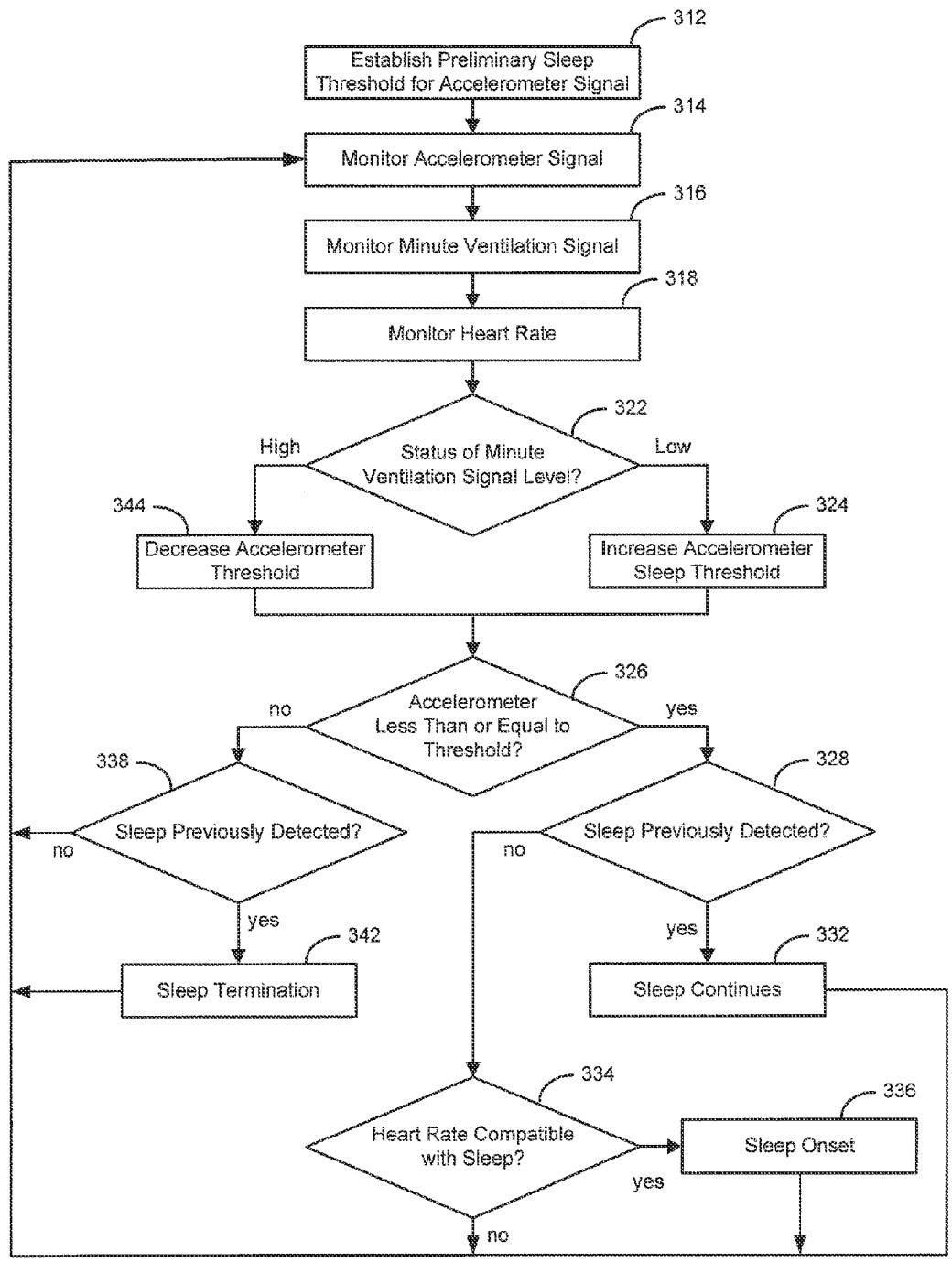
FIG. 3B is a flow chart illustrating a sleep detection method based on signals from an accelerometer and a minute ventilation sensor in accordance with embodiments of the present invention.

The flowchart illustrated in FIG. 3B is one example of an algorithmic approach to sleep detection that may be used in cooperation with detection of arousal from sleep in accordance with embodiments of the invention. In an exemplary methodology described below, detection of sleep is based in part on patient respiration. FIG. 2 illustrates normal breathing cycles. Respiration may be sensed, for example, by measuring the patient's transthoracic impedance. Transthoracic impedance increases with respiratory inspiration 220 and decreases with respiratory expiration 210. The impedance signal 200 is also proportional to the amount of air inhaled. Referring now to FIG. 2, a tranthoracic impedance signal 200 is illustrated. The impedance signal 200 may be developed, for example, using intracardiac impedance electrodes in combination with a CRM device.

The variations in impedance during respiration, identifiable as the peak-to-peak variation of the impedance signal 200, may be used to determine the respiration tidal volume. Tidal volume (TV) corresponds to the volume of air moved in a breath. Minute ventilation (MV) may also be determined, corresponding to the amount of air moved in a one minute.

In the flow chart of FIG. 3B, an accelerometer and a minute ventilation sensor are used to develop the first and second signals associated with sleep. A preliminary accelerometer signal sleep threshold is determined 312. For example, the preliminary sleep threshold may be determined from clinical data taken from a group of subjects or historical data taken from the patient over a period of time.

The activity level of the patient is monitored using an accelerometer 314 that may be incorporated into an implantable cardiac pacemaker as described above. Alternatively, the accelerometer may be attached externally to the patient. The patient's minute ventilation (MV) signal is monitored 316. The MV signal may be acquired, for example, based on the transthoracic impedance signal as described above using an implantable cardiac device. Other methods of determining the MV signal are also possible and are considered to be within the scope of this invention.

In this example, the accelerometer signal represents the sleep detection signal associated with the sleep threshold. The MV signal is the threshold adjustment signal used to adjust the sleep threshold. Heart rate is monitored 318 in this example to provide a sleep confirmation signal.

Threshold adjustment may be accomplished by using the patient's MV signal status 322 to moderate the accelerometer sleep threshold. If the patient's MV signal status 322 is low relative to an expected MV level associated with sleep, the accelerometer sleep threshold is increased 324. Similarly, if the patient's MV signal status 322 is high relative to an expected MV level associated with sleep, the accelerometer sleep threshold is decreased 344. Thus, when the patient's MV level is high, less activity is required to make the determination that the patient is sleeping. Conversely when the patient's MV level is relatively low, a higher activity level may result in detection of sleep. The use of two sleep-related signals to determine a sleep condition enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal status 322 is high relative to an expected MV level associated with sleep, the accelerometer sleep threshold is decreased 344. If the MV signal status 322 is low relative to an expected MV level associated with sleep, the accelerometer sleep threshold is increased 324.

If the sensed accelerometer signal is less than or equal to the adjusted sleep threshold, indicated by a yes at decision 326, and if the patient is not currently in a sleep state 328, then the patient's heart rate is checked 334 to confirm the sleep condition. If the patient's heart rate is compatible with sleep 334, then sleep onset is determined 336. If the patient's heart rate is incompatible with sleep, then the patient's sleep-related signals continue to be monitored.

If the accelerometer signal is less than or equal to the adjusted sleep threshold at decision 326, and if the patient is currently in a sleep state 328, then a continuing sleep state 332 is determined and the patient's sleep-related signals continue to be monitored for sleep termination to occur.

If the accelerometer signal is greater than the adjusted sleep threshold, as indicated by a no condition at decision 326, and the patient is not currently in a sleep state 338, then the patient's sleep-related signals continue to be monitored until sleep onset 336 is detected. If the accelerometer signal is greater than the adjusted sleep threshold at decision 326, and the patient is currently in a sleep state 338, then sleep termination is detected 342.

Figure 4:
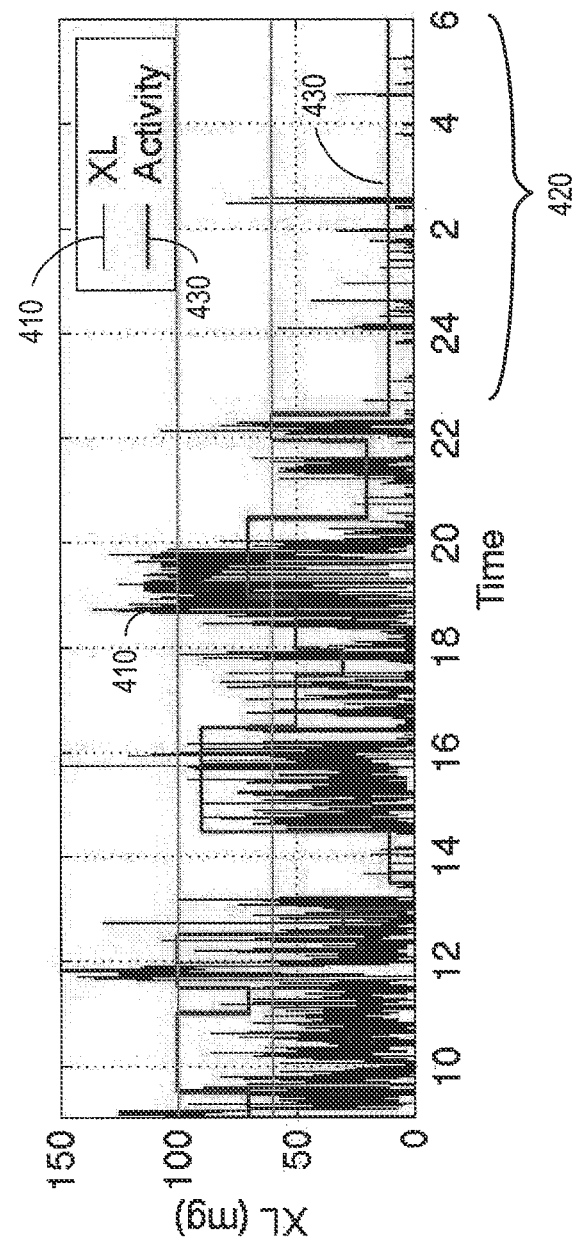
FIG. 4 is a graph of an accelerometer signal indicating patient activity level that may be used for sleep detection and arousal in accordance with embodiments of the present invention.

The graphs of FIGS. 4-7 illustrate sensor data, trends, and the adjustment of the accelerometer sleep thresholds using the MV signal. The relationship between patient activity and the accelerometer and MV signals is trended over a period of time to determine relative signal levels associated with a sleep condition. FIG. 4 illustrates an activity level 430 as indicated by an accelerometer signal 410 (the accelerometer signal 410 is represented in the graph legend as trace XL). The accelerometer signal 410 indicates a period of sleep 420 associated with a relatively low level of activity beginning at slightly before time 23:00 and continuing through time 6:00. The accelerometer trends may be used to establish a threshold for sleep detection. The activity level 430 may be derived, for example, by integrating the accelerometer signal 410 within a moving time window, where the length of the time window is adjusted to compensate for movement during sleep or other spurious activity or inactivity sources.

Figure 5:
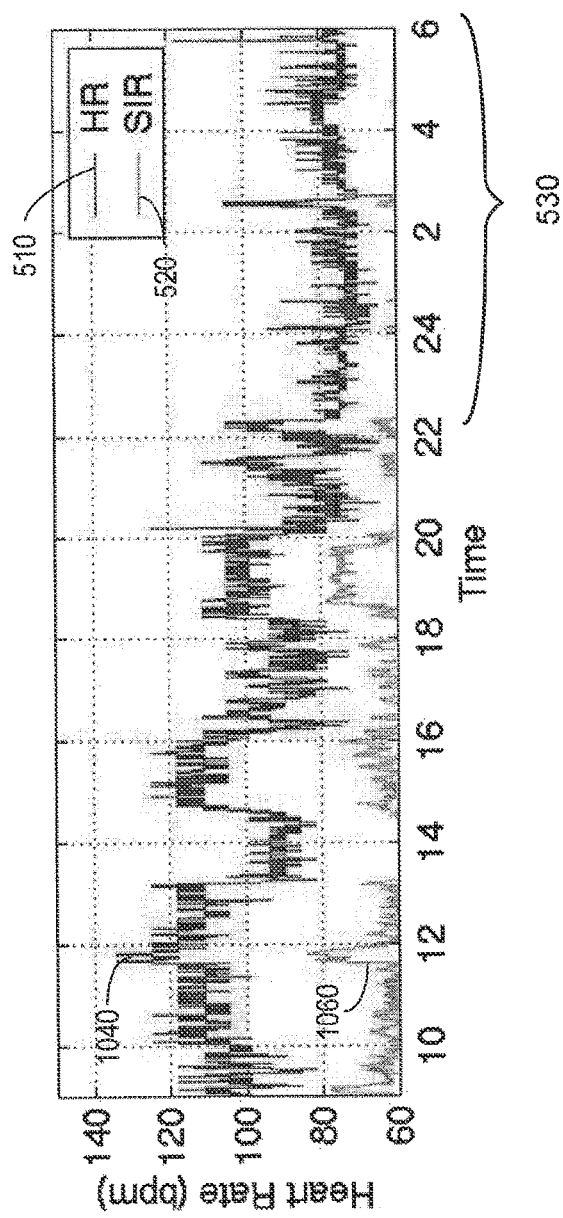
FIG. 5 is a graph of a patient's heart rate and sensor indicated rate that may be used for sleep detection and arousal in accordance with an embodiment of the present invention.

The patient's heart rate for the same time period illustrated in FIG. 4 is graphed in FIG. 5. A heart rate signal 510 appropriately tracks the activity level 430 (FIG. 4) indicated by the accelerometer, indicating a similar period 530 of low heart rate corresponding to sleep. A sensor indicated rate 520 is graphed in FIG. 5, and is represented in the graph legend as trace SIR. As illustrated in FIG. 5, the sensor indicated rate 520 may differ from the actual heart rate signal 510. For example, the sensor indicated rate 520 may be sensed from an implanted electrode or other sensor and correlates to the hemodynamic need of the patient.

Figure 6:
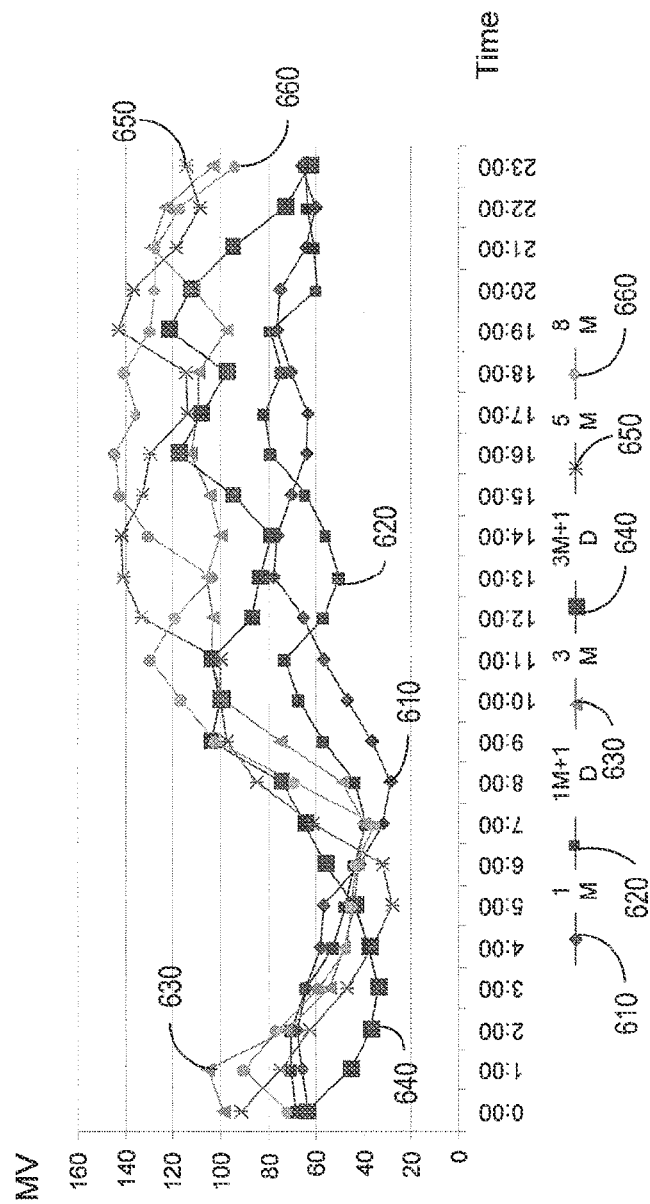
FIG. 6 is a graph of baseline trending for a minute ventilation (MV) signal used for sleep detection in accordance with embodiments of the present invention.

FIG. 6 is a graph of baseline trending for an MV signal. Historical data of minute ventilation of a patient is graphed over an 8 month period. In FIG. 6, a trace is provided for: one month as a trace 610; one month plus one day as a trace 620; three months as a trace 630; three month plus one day as a trace 640; five months as a trace 650; and eight months as a trace 660. The MV signal trending data is used to determine the MV signal level associated with sleep. In this example, a composite MV signal using the historical data indicates a roughly sinusoidal shape with the relatively low MV levels occurring approximately during the period from about hours 21:00 through 8:00. The low MV levels are associated with periods of sleep, particularly evident at about hours 3:00 through 6:00 in the graphs of FIG. 6, having The MV signal level associated with sleep may be used to implement sleep threshold adjustment as will be described further below and in association with FIG. 7.

Figure 7:
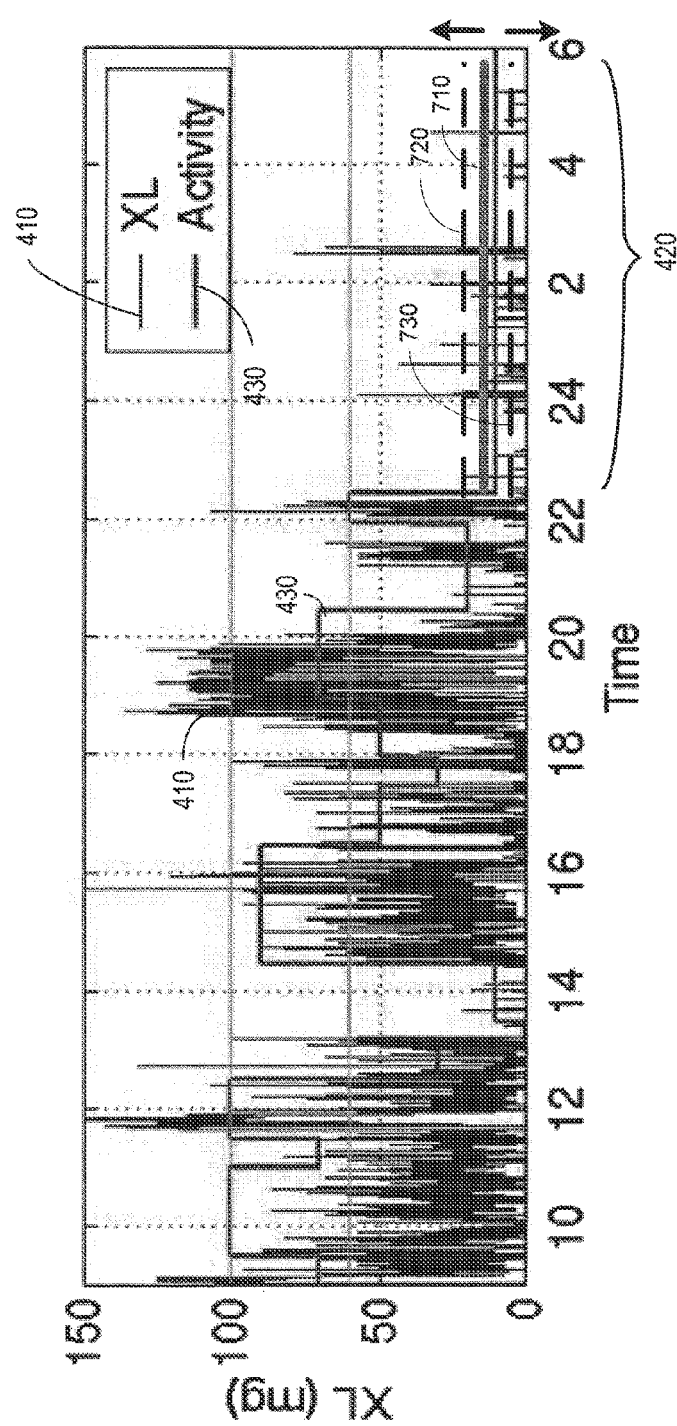
FIG. 7 illustrates adjustment of an accelerometer sleep threshold using an MV signal in accordance with embodiments of the present invention

FIG. 7 illustrates adjustment of the accelerometer sleep threshold using the MV signal. FIG. 7 is based on the graph of FIG. 4, including the activity level 430 as indicated by the accelerometer signal 410 (again, represented in the graph legend as trace XL). An initial sleep threshold 710 is established using the baseline accelerometer signal data acquired as discussed above. If the patient's MV signal is low relative to an expected MV level associated with sleep, the accelerometer sleep threshold is increased to an increased sleep threshold 720. If the patient's MV signal level is high relative to an expected MV level associated with sleep, the accelerometer sleep threshold is decreased to a decreased sleep threshold 730. When the patient's MV level is high, less activity detected by the accelerometer is required to make the determination that the patient is sleeping. However, if the patient's MV level is relatively low, a higher activity level may result in detection of sleep. The use of two sleep-related signals to adjust a sleep threshold for determining a sleep condition enhances the accuracy of sleep detection.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above.

Various embodiments of the invention involve the use of arousal detection cooperation with detection of sleep disorder events. In some implementations presented herein, arousal detection is used in cooperation with detection of sleep disordered breathing. Methods and systems for detecting disordered breathing, aspects of which may be utilized in connection with the embodiments presented herein, are described in commonly owned U.S. patent application Ser. No. 10/309,770, filed Dec. 4, 2002, now U.S. Pat. No. 7,252,640, and incorporated herein by reference.

Episodes of disordered breathing may be determined, for example, using the tranthoracic impedance signal, and/or other information available to the sleep disorder event detection circuitry. In one exemplary implementation, a disordered breathing event is declared when the patient's tidal volume (TV) falls below a threshold. For example, when the TV, as indicated by the transthoracic impedance signal, falls below a hypopnea threshold, then a hypopnea event is declared. In one implementation, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 8:
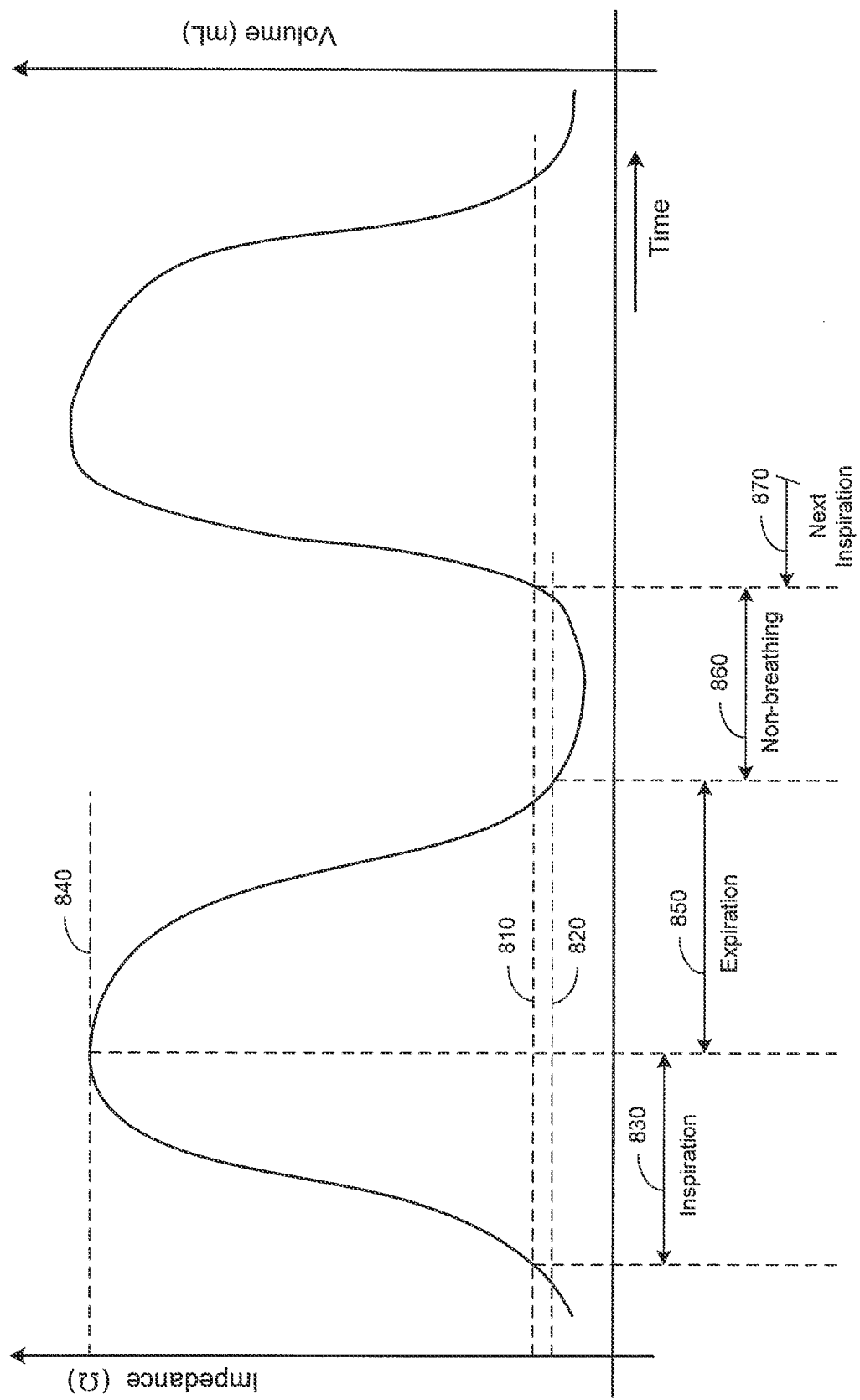
FIG. 8 is a respiration signal graph illustrating respiration intervals used for disordered breathing detection according to embodiments of the present invention.
Figure 9:
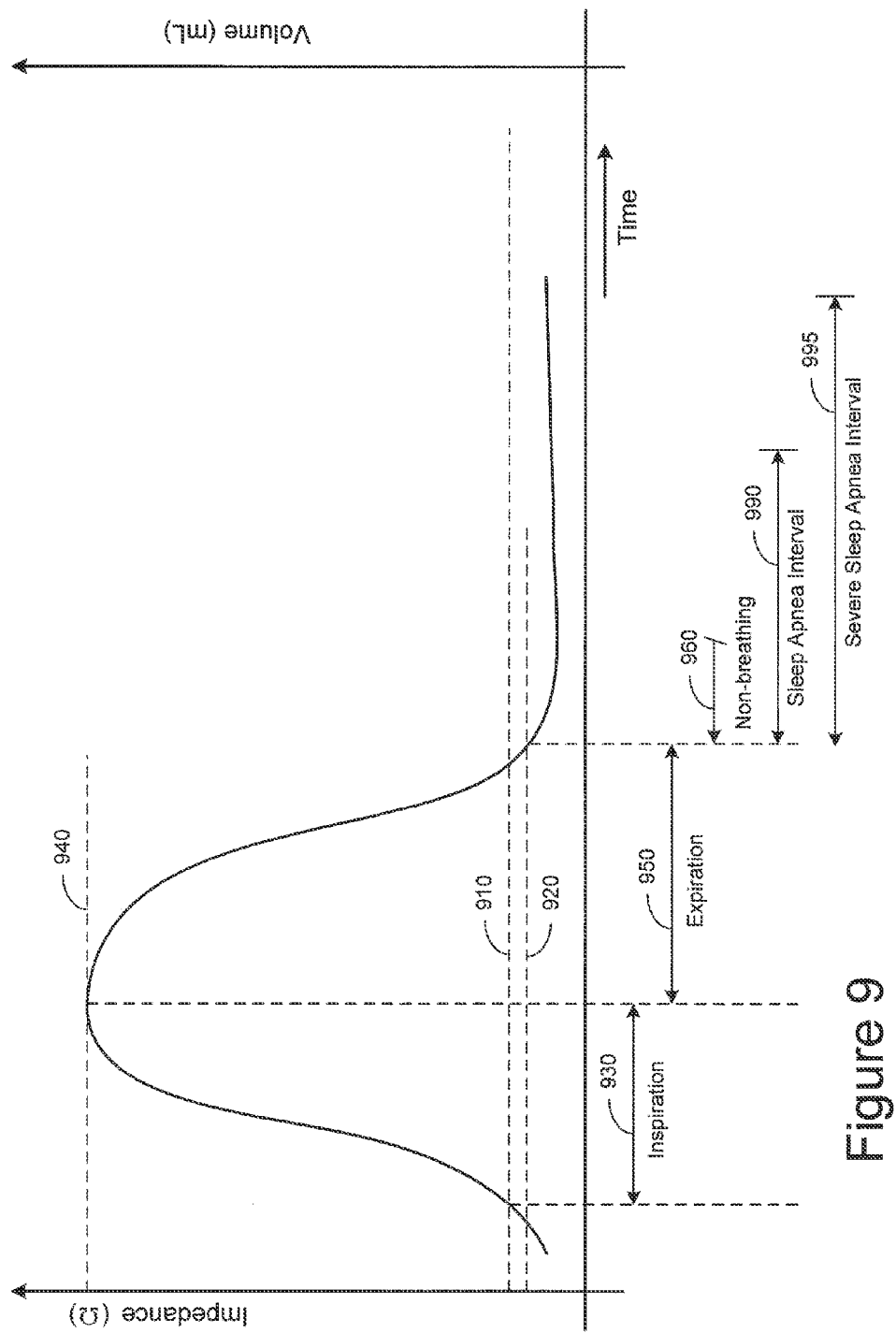
FIG. 9 is a graph of a respiration signal illustrating various intervals that may be used for detection of apnea in accordance with embodiments of the present invention.
Figure 10:
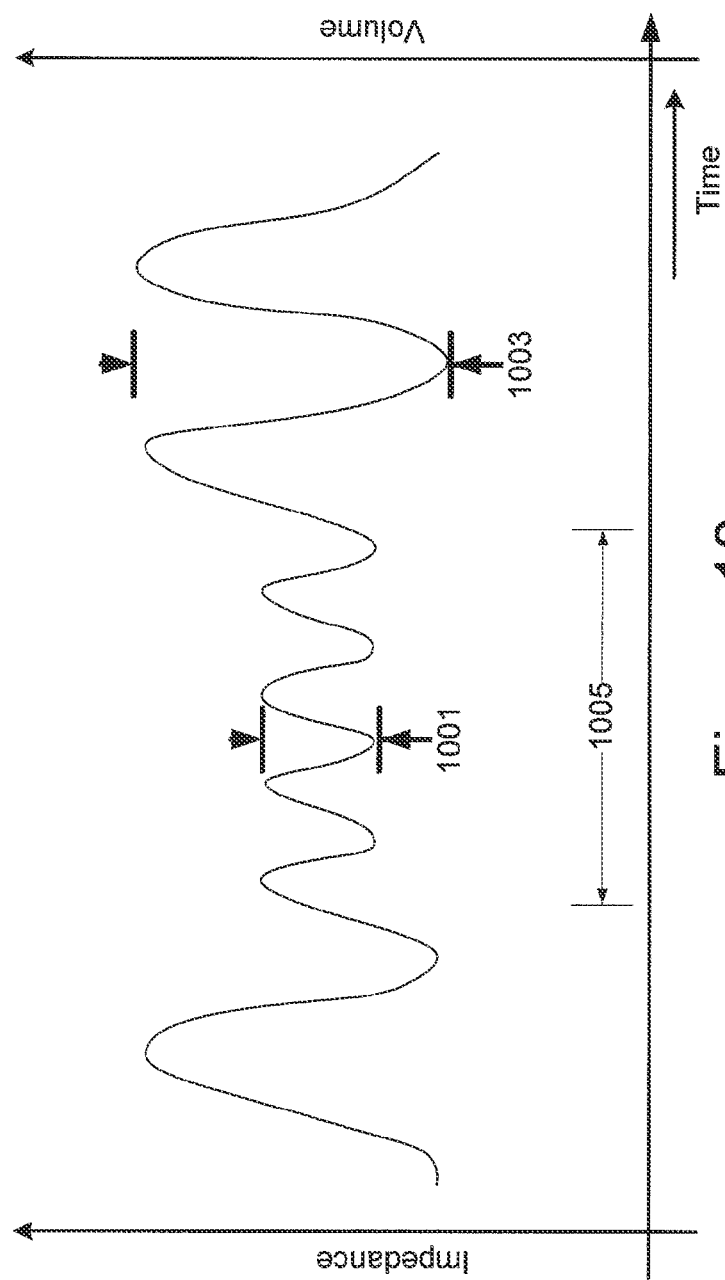
FIG. 10 is a respiration graph illustrating abnormally shallow respiration utilized in detection of disordered breathing in accordance with embodiments of the present invention.

FIGS. 8-10 are graphs of transthoracic impedance, similar to FIG. 2 previously described. FIG. 8 illustrates respiration intervals used for disordered breathing detection useful in accordance with embodiments of the present invention. Detection of disordered breathing may involve defining and examining a number of respiratory cycle intervals. A respiration cycle is divided into an inspiration period 830 corresponding to the patient inhaling, an expiration period 850, corresponding to the patient exhaling, and a non-breathing period 860 occurring between inhaling and exhaling. Respiration intervals are established using an inspiration threshold 810 and an expiration threshold 820. The inspiration threshold 810 marks the beginning of an inspiration period 830 and is determined by the transthoracic impedance signal 200 rising above the inspiration threshold 810. The inspiration period 830 ends when the transthoracic impedance signal 200 is a maximum 840.

The maximum transthoracic impedance signal 840 corresponds to both the end of the inspiration interval 830 and the beginning of an expiration interval 850. The expiration interval 850 continues until the transthoracic impedance 200 falls below an expiration threshold 820. A non-breathing interval 860 starts from the end of the expiration period 850 and continues until the beginning of a next inspiration period 870.

Detection of sleep apnea and severe sleep apnea is illustrated in FIG. 9. The patient's respiration signals are monitored and the respiration cycles are defined according to an inspiration 930, an expiration 950, and a non-breathing 960 interval as described in connection with FIG. 8. A condition of sleep apnea is detected when a non-breathing period 960 exceeds a first predetermined interval 990, denoted the sleep apnea interval. A condition of severe sleep apnea is detected when the non-breathing period 960 exceeds a second predetermined interval 995, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of disordered breathing characterized by abnormally shallow breathing. FIG. 10 is a graph of tidal volume derived from transthoracic impedance measurements. The graph of FIG. 10 illustrating the tidal volume of a hypopnea episode may be compared to the tidal volume of a normal breathing cycle illustrated previously in FIG. 2, which illustrated normal respiration tidal volume and rate. As shown in FIG. 10, hypopnea involves a period of abnormally shallow respiration.

Hypopnea is detected by comparing a patient's respiratory tidal volume 1003 to a hypopnea tidal volume 1001. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 10, a hypopnea episode 1005 is identified when the average tidal volume is significantly below the normal tidal volume. In the example illustrated in FIG. 10, the normal tidal volume during the breathing process is identified as the peak-to peak value identified as the respiratory tidal volume 1003. The hypopnea tidal volume during the hypopnea episode 1005 is identified as hypopnea tidal volume 1001. For example, the hypopnea tidal volume 1001 may be about 50% of the respiratory tidal volume 1003. The value 50% is used by way of example only, and determination of thresholds for hypopnea events may be determined as any value appropriate for a given patient.

Figure 11:
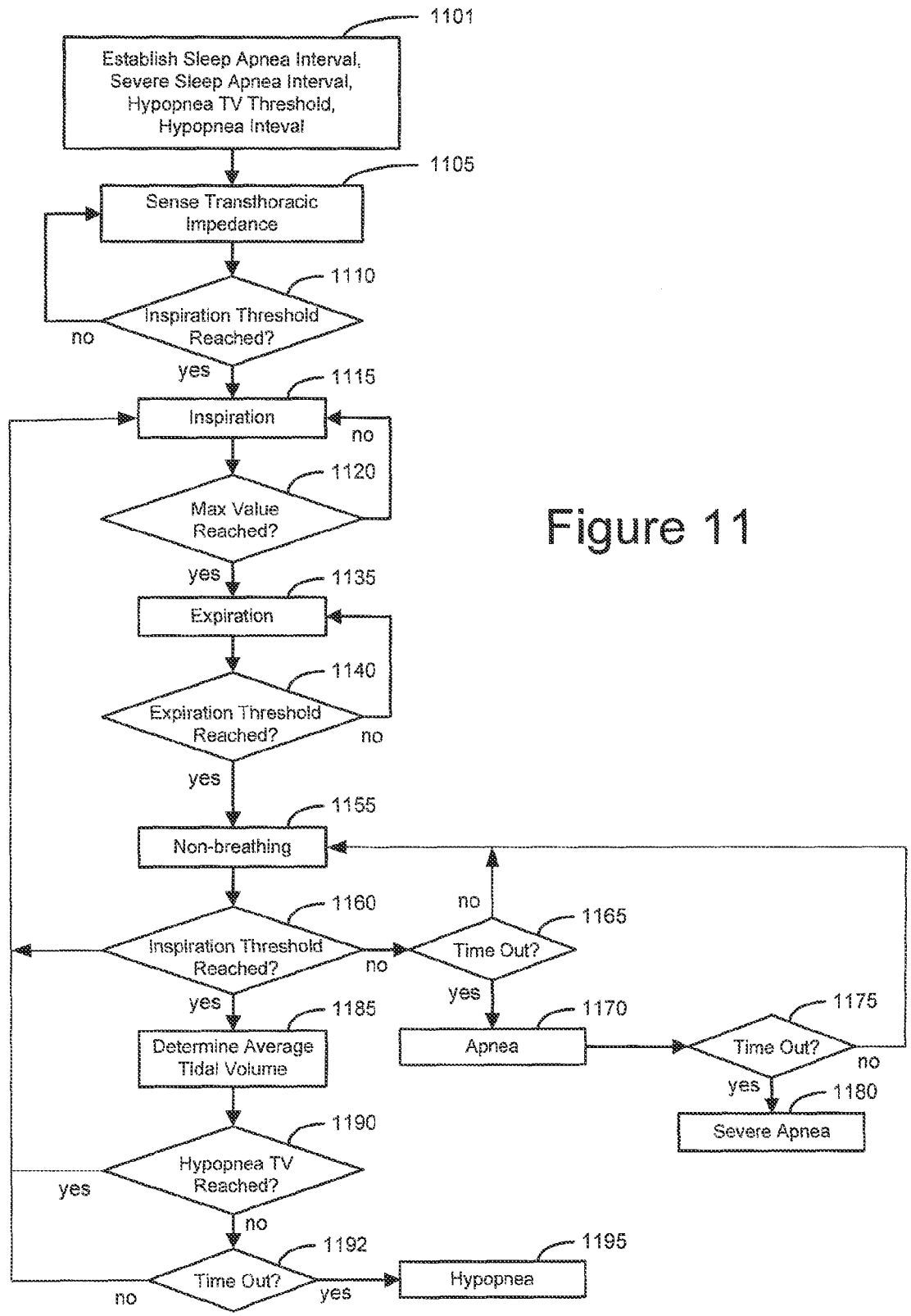
FIG. 11 is a flow chart illustrating a method of apnea and/or hypopnea detection according to embodiments of the present invention.

In the example above, if the tidal volume falls below about 50% of the respiratory tidal volume 1003, the breathing episode may be identified as a hypopnea event. The period of time that the patient's tidal volume remains below about 50% of the respiratory tidal volume 1003 defines the period of the hypopnea event. FIG. 11 is a flow chart illustrating a method of apnea and/or hypopnea detection useful in accordance with embodiments of the present invention. Various parameters are established 1101 before analyzing the patient's respiration for disordered breathing episodes, including, for example, inspiration and expiration thresholds, sleep apnea interval, severe sleep apnea interval, and hypopnea tidal volume (TV) threshold.

The patient's transthoracic impedance is measured 1105 as described in more detail above. If the transthoracic impedance exceeds 1110 the inspiration threshold, the beginning of an inspiration interval is detected 1115. If the transthoracic impedance remains below 1110 the inspiration threshold, then the impedance signal is checked 1105 periodically until inspiration 1115 occurs.

During the inspiration interval, the patient's transthoracic impedance is monitored until a maximum value of the transthoracic impedance is detected 1120. Detection of the maximum value signals an end of the inspiration period and a beginning of an expiration period 1135.

The expiration interval is characterized by decreasing transthoracic impedance. When, at determination 1140, the transthoracic impedance falls below the expiration threshold, a non-breathing interval is detected 1155.

If the transthoracic impedance determination 1160 does not exceed the inspiration threshold within a first predetermined interval, denoted the sleep apnea interval 1165, then a condition of sleep apnea is detected 1170. Severe sleep apnea 1180 is detected if the non-breathing period extends beyond a second predetermined interval, denoted the severe sleep apnea interval 1175.

When the transthoracic impedance determination 1160 exceeds the inspiration threshold, the tidal volume from the peak-to-peak transthoracic impedance is calculated, along with a moving average of past tidal volumes 1185. The peak-to-peak transthoracic impedance provides a value proportional to the tidal volume of the respiration cycle. This value is compared at determination 1190 to a hypopnea tidal volume threshold. If, at determination 1190, the peak-to-peak transthoracic impedance is consistent with the hypopnea tidal volume threshold for a predetermined time 1192, then a hypopnea cycle 1195 is detected.

In some exemplary implementations presented herein, arousal detection is used in cooperation with detection of nocturnal disordered movement events. Restless leg movement syndrome and periodic limb movement disorder are closely associated disorders also known as Myoclonus and Ekbom Syndrome, respectively. Restless Leg Syndrome (RLS) and Periodic Limb Movement Disorder (PLMD) affect 2-8% of the population in the United States. Both conditions are characterized by involuntary movements of the limbs, most typically the legs.

Restless Leg Syndrome (RLS) is a disorder that occurs during periods of wakefulness. Periodic Limb Movement Disorder (PLMD) occurs during sleep or in transitions from wake to sleep or sleep to wake. Patients with RLS or PLMD may suffer twitching, tingling, aching, burning, itching, or pulling sensations in their arms and/or legs. Because RLS patients may also suffer from sleep-related PLMD, these patients are often aroused from sleep, and their ability to return to sleep is delayed by RLS.

RLS patients are unable to sit still and may have to remain active to relieve limb discomfort. For patients suffering from RLS, relaxation and passive activities become increasingly problematic, adversely affecting the quality of life.

For both PLMD and RLS patients, sleep quality deteriorates. When a patient tries to fall asleep, the leg discomfort begins. In severe cases, patients only sleep a few hours at night, resulting in excessive daytime sleepiness and disruption of the normal daily routine. RLS and PLMD patients often complain of irritability, anxiety, and depression. The severity of RLS and/or PLMD ranges from infrequent minor discomfort to daily agony that leads some patients to contemplate suicide.

Symptoms of PLMD may come and go through the night and over the course of one's life. PLMD episodes may last a few minutes or several hours. There may be an interval of days, weeks or months between episodes. PLMD patients may experience sudden but rhythmic limb jerks occurring periodically, e.g., every 20 to 40 seconds. PLMD episodes may be seen primarily in the first third of the night, during non-REM sleep. Patients with RLS often have PLMD, but patients with PLMD do not always have RLS. Polysomnographic studies indicate that about 70% to 90% of patients with RLS have PLMD.

PLMD movements may be characterized, for example, by periodic flexion of one or both legs involving bending at the hip and knee with upward bending of the foot and the great toe, resembling a flexion reflex. A normal healthy person may have five of these movements per hour. The diagnosis of PLMD is given when more than five movements per hour occur.

Both genders are affected, with a slightly higher incidence in women. These conditions are seen more commonly with advancing age. The prevalence of PLMD or RLS is 2% of the population of ages less than 30, 5% of ages 30 to 50, and 25% of ages 50-60. The highest prevalence is seen in age 65 or older, with 44% of the population affected. While usually diagnosed in older groups, these disorders may be traced to childhood. Hyperactive, fidgeting children or youths often labeled with "growing pains" may actually be showing the early manifestations of PLMD and RLS.

In accordance with embodiments of the invention, nocturnal disordered movement events such as bruxism events and PLMD events, for example, may be detected using a system that is fully or partially implantable. With reference to FIG. 1D an implantable medical device, e.g., a CRM device, incorporates a sleep disorder event detector 164 that may include a movement disorder detector. One or more sleep disorder sensors 165, e.g., movement sensors may be coupled to the sleep disorder event detector 164 within the implantable device 161.

The sleep disorder sensors 165 may include any sensor or any combination of sensors capable of detecting motion and/or muscle activity associated with motion. For example, the patient's movements may be detected using one or more accelerometers, one or more EMG sensors, and/or a combination of one or more accelerometers and one or more EMG sensors.

In one embodiment, one or more movement sensors (e.g., accelerometers and/or sub-movement EMG sensors) are coupled to the patient at appropriate locations to detect movements of the extremities, e.g., limb movements, or other movements. Signals from the sleep disorder sensors 165 are received and processed by the sleep disorder event detector 164 in the implantable device 161. The sleep disorder event detector 164 may cooperate with a memory in a monitoring unit 167 to store information about the detected movements. Movement information may be stored, trended, displayed, and/or transmitted to a separate device, such as an APM system 180 or a programmer 190 for further operations.

In another embodiment, illustrated in FIG. 1D, one or more movement sensors 165 are coupled to a sleep disorder event detector 164 within the implantable device 161, as previously discussed. The implantable device 161 also includes a therapy unit 175 that receives movement information from the sleep disorder event detector 164, the arousal detector 162, and/or other components of the implantable device 161. The therapy unit may provide therapy, e.g., drug therapy, for various movement disorders such as RLS and/or PLMD.

In one example, the movement sensors 165 may include one of more EMG sensors placed on or in the anterior tibialis. Typical EMG bursts due to PLMD movements may last between 0.5-5 seconds and may recur every 20-40 seconds, for example. The sleep disorder event detector 164 may detect PLMD if at least about 40 EMG bursts are detected within an 8 hour sleep period, for example. Sleep disruption caused by the PLMD movements may be determined by any or a combination of the sleep detection techniques described herein, including, for example, electrical muscle activity (EMG) sensing, brain wave (EEG) sensing and/or a combination of respiration (MV) and activity sensing, among others. Movement disorder information may be downloaded to a programmer 190, an APM system 180, or other therapeutic or diagnostic device.

Arousal detection with or without sleep disorder event detection may be used in connection with delivering therapy to the patient. In one implementation, detection of an excessive number of arousals may trigger therapy adjustments that promote more restful sleep. Some examples of therapies that may be used to treat patients with sleep disorders are outlined below.

Drug therapy has been used to treat movement disorders and sleep disordered breathing. Disordered breathing may also be treated using oral appliances, electrical stimulation, respiration therapy, and surgery, for example. Obstructive apnea is caused by an obstruction in the patient's airway. Obstructive apnea has been associated with prolapse of the tongue and the surrounding structure into the pharynx during sleep, thus occluding the respiratory pathway. Central apnea is a neurological disorder causing a derangement of the respiratory drive signals, typically without any mechanical obstruction or other ventilatory defects. A commonly prescribed treatment for both obstructive and central apneas is positive airway pressure. Positive air pressure devices deliver air pressure to the patient, often through a facial or nasal mask worn by the patient. In the case of obstructive apnea, the application of a positive airway pressure keeps the patient's throat open, reducing the occlusion causing the apnea.

Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal (HG) nerve innervates the protrusor and retractor tongue muscles. An appropriately applied electrical stimulation to the hypoglossal nerve, for example, may prevent backward movement of the tongue, thus preventing the tongue from obstructing the airway.

Central sleep apnea may also be treated by phrenic nerve pacing, also referred to as diaphragmatic pacing. Phrenic nerve pacing uses an electrode implanted in the chest to stimulate the phrenic nerve. The phrenic nerve is generally known as the motor nerve of the diaphragm. It runs through the thorax, along the heart, and then to the diaphragm. Diaphragmatic pacing is the use of electronic stimulation of the phrenic nerve to control the patient's diaphragm and induce a respiratory cycle. Pacing the phrenic nerve may be accomplished by surgically placing a nerve cuff on the phrenic nerve, and then delivering an electric stimulus. The electric stimulus of the phrenic nerve then causes the diaphragm to induce a respiratory cycle.

Recently, cardiac electrical stimulation therapy has been used as a therapy for disordered breathing. Cardiac electrical stimulation is typically implemented using an implanted electrical pulse generator coupled to endocardiac leads inserted into one or more heart chambers.

Cardiac electrical stimulation therapy may involve pacing one or more chambers of the heart. Pacing therapy may involve, for example, pacing one or more atria and/or one or more ventricles. In one implementation, overdrive pacing is used to mitigate disordered breathing.

Therapy for disordered breathing may involve non-excitatory electrical stimulation of one or more heart chambers, e.g., the left and/or right ventricles, or other cardiac sites. Non-excitatory electrical stimulation may be delivered during absolute refractory periods of the cardiac tissue, for example, to improve cardiac contractility. The non-excitatory stimulation therapy may be used alone or in combination with pacing therapy to provide a comprehensive therapy regimen for patients with CHF and disordered breathing such as Cheyne-Stokes respiration.

Some patients may benefit from a therapy regimen that includes a combination of the therapy techniques outlined above. For example, disordered breathing therapy may involve a combination of cardiac electrical stimulation therapy and external respiration therapy.

Figure 12:
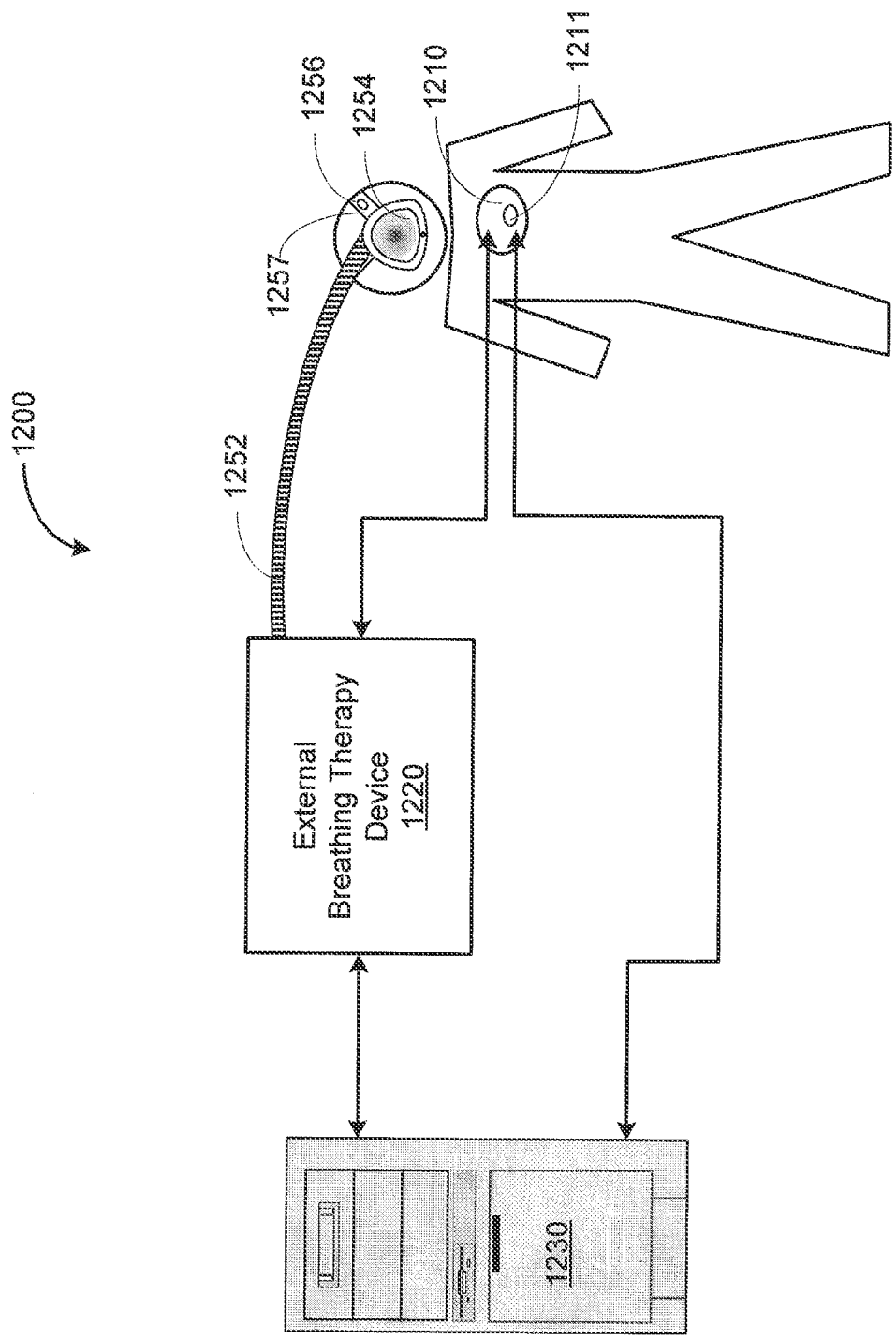
FIG. 12 illustrates a medical system including an implantable cardiac rhythm management device that cooperates with a patient-external respiration therapy device to provide coordinated patient monitoring, diagnosis and/or therapy in accordance with an embodiment of the present invention.

In the example illustrated in FIG. 12, a mechanical respiration therapy device 1220 providing positive airway pressure therapy cooperates with an implantable cardiac device, e.g., cardiac rhythm management system (CRM) device 1210 providing cardiac electrical stimulation therapy. Positive airway pressure devices may be used to deliver a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. All types of positive airway pressure devices are referred to generically herein as xPAP devices.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any device using forms of positive airway pressure (and negative pressure when necessary), whether continuous or otherwise.

The xPAP device 1220 develops a positive air pressure that is delivered to the patient's airway through a tube system 1252 and a mask assembly 1254 connected to the xPAP device 1220. The mask assembly 1254 may include EEG sensors, such as one or more EEG sensors 1256 attached to a strap 1257 that is placed around the head of the patient, or electrocardiogram (ECG) sensors attached to the mask or strap. In one configuration, for example, the positive airway pressure provided by the xPAP device 1220 acts as a pneumatic splint keeping the patient's airway open and reducing the severity and/or number of occurrences of disordered breathing due to airway obstruction.

The CRM 1210 may deliver cardiac electrical stimulation therapy for disordered breathing and/or for cardiac dysfunctions such as bradycardia, tachycardia and congestive heart failure. The CRM device 1210 may include a number of sensors, such as cardiac sense electrodes, transthoracic impedance sensors, and/or patient activity sensors that may be used in connection with arousal detection, disordered breathing detection, sleep detection and/or sleep disorder event detection. In one embodiment, an arousal sensor e.g., an EMG sensor 1211, is positioned on the housing of the CRM device 1210.

The CRM 1210 and xPAP 1220 devices may communicate directly through a wireless communications link, for example. Alternatively, or additionally, the CRM 1210 and xPAP 1220 devices may communicate with and/or through an APM device such as an APM system 1230, as will be described further below. The CRM 1210 may include a lead system having electrodes for electrically coupling to the heart, for example.

In the embodiment depicted in FIG. 12, the EMG sensor 1211 and/or the EEG sensor 1256 may communicate with an arousal detector that may be housed within the CRM device 1210 or within the xPAP device 1220, for example. The arousal detector detects arousals from sleep based on signals from one or both of the EEG sensor 1256 and the EMG sensor 1211. Information about the detected arousals from sleep may be communicated to the CRM 1210 and/or the xPAP 1220. The arousal information may be used to initiate, terminate or adjust the cardiac electrical stimulation and/or respiration therapy delivered to the patient.

Although FIG. 12 illustrates a CRM device 1210 used with a xPAP device 1220 to provide coordinated patient monitoring, diagnosis and/or therapy, any number of patient-internal and patient-external medical devices may be included in a medical system in accordance with the present invention. For example, a drug delivery device, such as a drug pump or controllable nebulizer, may be included in the system 1200. The drug delivery device may cooperate with either or both of the CRM device 1210 and the xPAP device 1220 and may contribute to the patient monitoring, diagnosis, and/or therapeutic functions of the medical system 1200.

Figure 13:
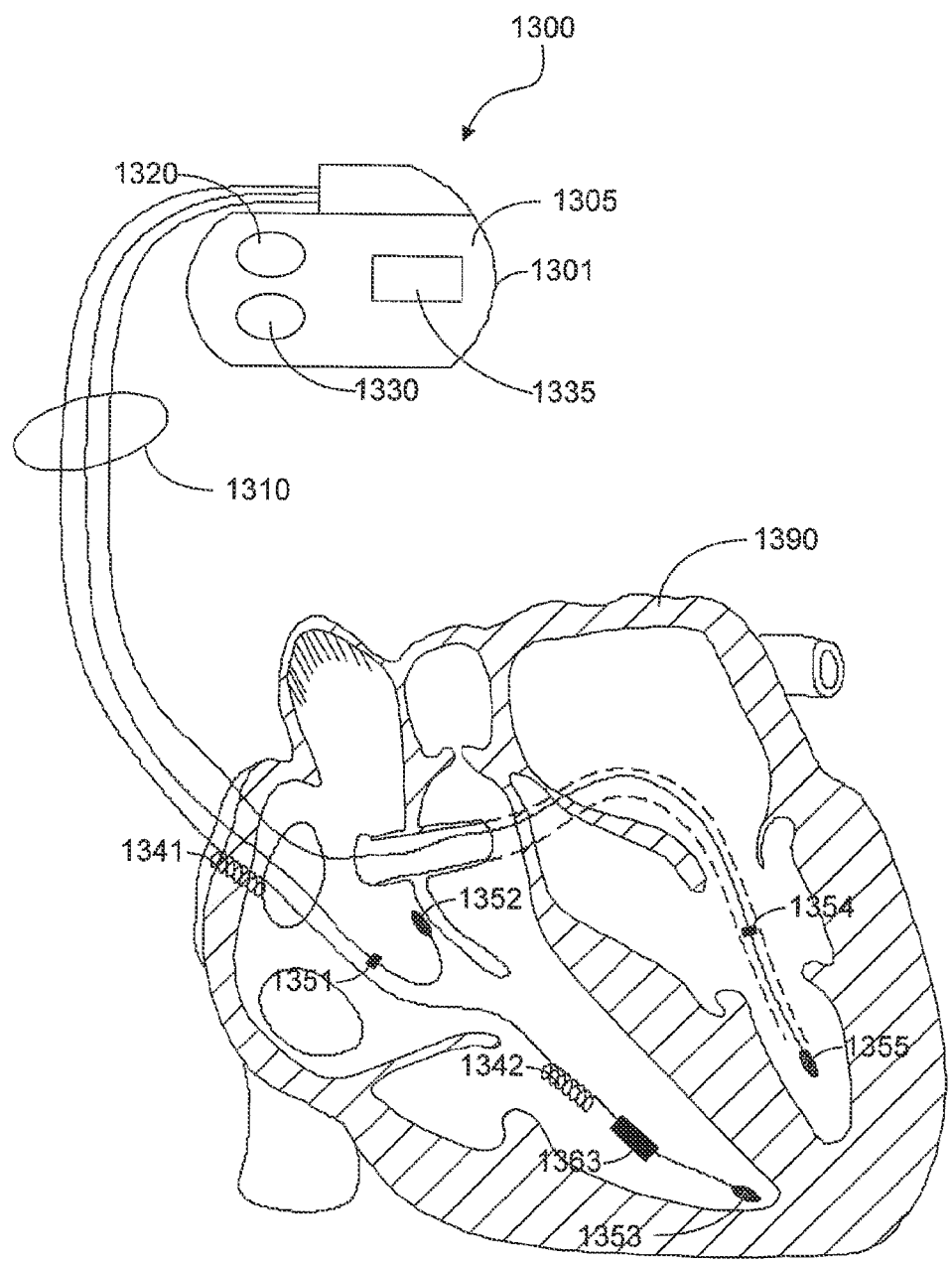
FIG. 13 is an illustration of an implantable cardiac device including a lead assembly shown implanted in a sectional view of a heart, the device used in connection with arousal detection in accordance with embodiments of the present invention.

FIG. 13 is a partial view of an implantable device that may include circuitry for autonomic arousal detection in accordance with embodiments of the invention. In this example, an arousal detector 1335 is configured as a component of a pulse generator 1305 of a cardiac rhythm management (CRM) device 1300. The implantable pulse generator 1305 is electrically and physically coupled to an intracardiac lead system 1310. The arousal detector 1335 may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 1310 are inserted into the patient's heart 1390. The intracardiac lead system 1310 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 1301 of the pulse generator 1305 may optionally serve as a can electrode.

Communications circuitry is disposed within the housing 1301, facilitating communication between the pulse generator 1305 including the arousal detector 1335 and an external device, such as a sleep disordered breathing therapy device and/or APM system. The communications circuitry can also facilitate unidirectional or bidirectional communication with one or more implanted, external, cutaneous, or subcutaneous physiologic or non-physiologic sensors, patient-input devices and/or information systems.

The pulse generator 1305 may optionally incorporate a EMG sensor 1320 disposed on the housing 1301 of the pulse generator 1305. The EMG sensor may be configured, for example, to sense myopotentials of the patient's skeletal muscle in the pectoral region. Myopotential sensing may be used in connection with arousal detection as described in more detail herein.

The pulse generator 1305 may further include a sensor configured to detect patient motion. The motion detector may be implemented as an accelerometer positioned in or on the housing 1301 of the pulse generator 1305. If the motion detector is implemented as an accelerometer, the motion detector may also provide acoustic information, e.g. rales, coughing, S1-S4 heart sounds, cardiac murmurs, and other acoustic information.

The lead system 1310 of the CRM device 1300 may incorporate a transthoracic impedance sensor that may be used to acquire the patient's cardiac output, or other physiological conditions related to the patient's autonomic arousal response. The transthoracic impedance sensor may include, for example, one or more intracardiac electrodes 1341, 1342, 1351-1355, 1363 positioned in one or more chambers of the heart 1390. The intracardiac electrodes 1341, 1342, 1351-1355, 1361, 1363 may be coupled to impedance drive/sense circuitry 1330 positioned within the housing of the pulse generator 1305.

The impedance signal may also be used to detect the patient's respiration waveform and/or other physiological changes produce a change in impedance, including pulmonary edema, heart size, cardiac pump function, etc. The respiratory and/or pacemaker therapy may be altered on the basis of the patient's heart condition as sensed by impedance.

In one example, the transthoracic impedance may be used to detect the patient's respiratory waveform. A voltage signal developed at the impedance sense electrode 1352, illustrated in FIG. 2, is proportional to the patient's transthoracic impedance and represents the patient's respiration waveform. The transthoracic impedance increases during respiratory inspiration and decreases during respiratory expiration. The transthoracic impedance may be used to determine the amount of air moved in one breath, denoted the tidal volume and/or the amount of air moved per minute, denoted the minute ventilation. A normal "at rest" respiration pattern, e.g., during non-REM sleep, includes regular, rhythmic inspiration-expiration cycles without substantial interruptions, as indicated in FIG. 2.

Returning to FIG. 13, the lead system 1310 may include one or more cardiac pace/sense electrodes 1351-1355 positioned in, on, or about one or more heart chambers for sensing electrical signals from the patient's heart 1390 and/or delivering pacing pulses to the heart 1390. The intracardiac sense/pace electrodes 1351-1355, such as those illustrated in FIG. 13, may be used to sense and/or pace one or more chambers of the heart, including the left ventricle, the right ventricle, the left atrium and/or the right atrium. The lead system 1310 may include one or more defibrillation electrodes 1341, 1342 for delivering defibrillation/cardioversion shocks to the heart.

The pulse generator 1305 may include circuitry for detecting cardiac arrhythmias and/or for controlling pacing or defibrillation therapy in the form of electrical stimulation pulses or shocks delivered to the heart through the lead system 1310. Arousal detection circuitry 1335 may be housed within the housing 1301 of the pulse generator 1305. The arousal detection circuitry 1335 may be coupled to various sensors, including the transthoracic impedance sensor 1330, EMG sensor 1320, EEG sensors, cardiac electrogram sensors, nerve activity sensors, and/or other sensors capable of sensing physiological signals modulated by the patient's autonomic arousal response.

The arousal detector 1335 may be coupled to a sleep disorder detector configured to detect sleep disorders such as disordered breathing, and/or movement disorders. The arousal detector and the sleep disorder detector may be coupled to a processor that may use information from the arousal detector and the sleep disorder detector to associate sleep disorder events with arousal events. The processor may trend the arousal events, associate the sleep disorder events with arousal events, and/or use the detection of the arousal events and/or the sleep disorder events for a variety of diagnostic purposes. The sleep disorder detector and/or the processor may also be configured as a component of the pulse generator 1305 and may be positioned within the pulse generator housing 1301. In one embodiment, information about the arousal events and/or the sleep disorder events may be used to adjust therapy delivered by the CRM device 1300 and/or other therapy device.

In addition to the EMG sensor, the cardiac sensors and the impedance sensor described above, various other sensors, including, for example, EEG sensors, accelerometers, posture sensors, proximity sensors, electrooculogram (EOG) sensors, photoplethymography sensors, blood pressure sensors, peripheral arterial tonography sensors, and/or other sensors useful in detecting autonomic arousal events and/or sleep disorder events may also be coupled to the CRM device 1300.

Figure 14:
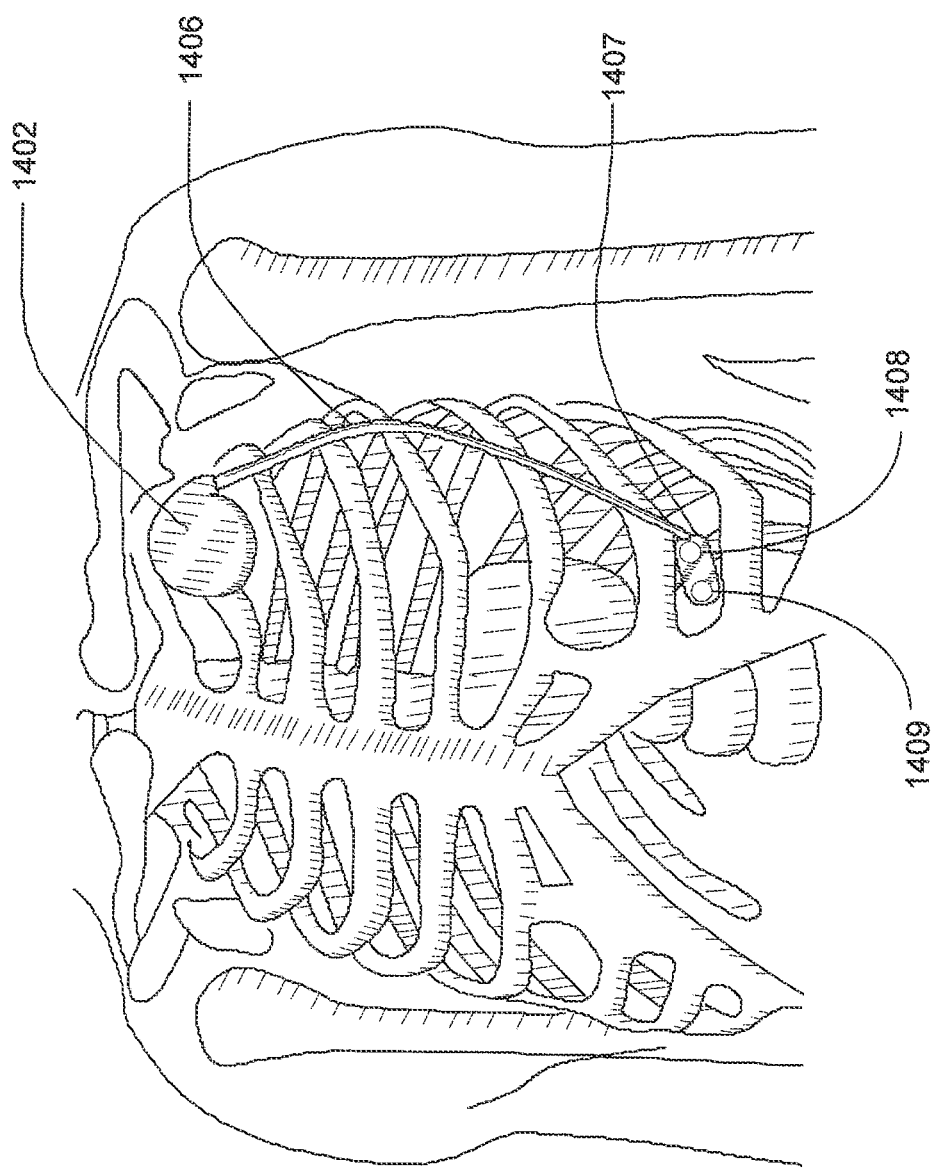
FIG. 14 is an illustration of a thorax having an implanted subcutaneous medical device that may be used in connection with arousal detection in accordance with an embodiment of the present invention.

FIG. 14 is a diagram illustrating an implantable transthoracic cardiac device that may be used in connection with detection of arousals from sleep in accordance with embodiments of the invention. The implantable device illustrated in FIG. 14 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

In accordance with one embodiment, an arousal sensor may be positioned on housing 1402, lead assembly 1406, or subcutaneous electrode assembly 1407 of the ITCS device. An arousal detector may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 14, a subcutaneous electrode assembly 1407 can be positioned under the skin in the chest region and situated distal from the housing 1402. The subcutaneous and, if applicable, housing electrode(s) can be positioned about the heart at various locations and orientations, such as at various anterior and/or posterior locations relative to the heart. The subcutaneous electrode assembly 1407 is coupled to circuitry within the housing 1402 via a lead assembly 1406. One or more conductors (e.g., coils or cables) are provided within the lead assembly 1406 and electrically couple the subcutaneous electrode assembly 1407 with circuitry in the housing 1402. One or more sense, sense/pace or defibrillation electrodes can be situated on the elongated structure of the electrode support, the housing 1402, and/or the distal electrode assembly (shown as subcutaneous electrode assembly 1407 in the configuration shown in FIG. 14).

It is noted that the electrode and the lead assemblies 1407, 1406 can be configured to assume a variety of shapes. For example, the lead assembly 1406 can have a wedge, chevron, flattened oval, or a ribbon shape, and the subcutaneous electrode assembly 1407 can comprise a number of spaced electrodes, such as an array or band of electrodes. Moreover, two or more subcutaneous electrode assemblies 1407 can be mounted to multiple electrode support assemblies 1406 to achieve a desired spaced relationship amongst subcutaneous electrode assemblies 1407.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent application Ser. No. 10/820,642 filed Apr. 8, 2004, now U.S. Pat. No. 7,570,997, and U.S. patent application Ser. No. 10/821,248, filed Apr. 8, 2004, published as U.S. Published Patent Application No. 2004-0215240, now abandoned, which are incorporated herein by reference.

The housing of the ITCS device may incorporate components of a arousal detection system including one or more of arousal detection circuitry, sleep detection circuitry, sleep disorder event detection circuitry, monitoring unit, for example as described in connection with FIG. 1D.

In one implementation, the ITCS device may include an impedance sensor configured to sense the patient's transthoracic impedance. The impedance sensor may include the impedance drive/sense circuitry incorporated with the housing 1402 of the ITCS device and coupled to impedance electrodes positioned on the can or at other locations of the ITCS device, such as on the subcutaneous electrode assembly 1407 and/or lead assembly 1406. In one configuration, the impedance drive circuitry generates a current that flows between a subcutaneous impedance drive electrode 1409 and a can electrode on the primary housing 1402 of the ITCS device. The voltage at a subcutaneous impedance sense electrode 1408 relative to the can electrode changes as the patient's transthoracic impedance changes. The voltage signal developed between the impedance sense electrode and the can electrode is sensed by the impedance drive/sense circuitry.

Communications circuitry is disposed within the housing 1402 for facilitating communication between the ITCS device and an external communication device, such as a portable or bed-side communication station, patient-carried/worn communication station, external programmer, APM system, or separate therapy device for example. The communications circuitry can also facilitate unidirectional or bidirectional communication with one or more external, cutaneous, or subcutaneous physiologic or non-physiologic sensors that may be used in connection with arousal detection in accordance with embodiments of the invention.

Figure 15:
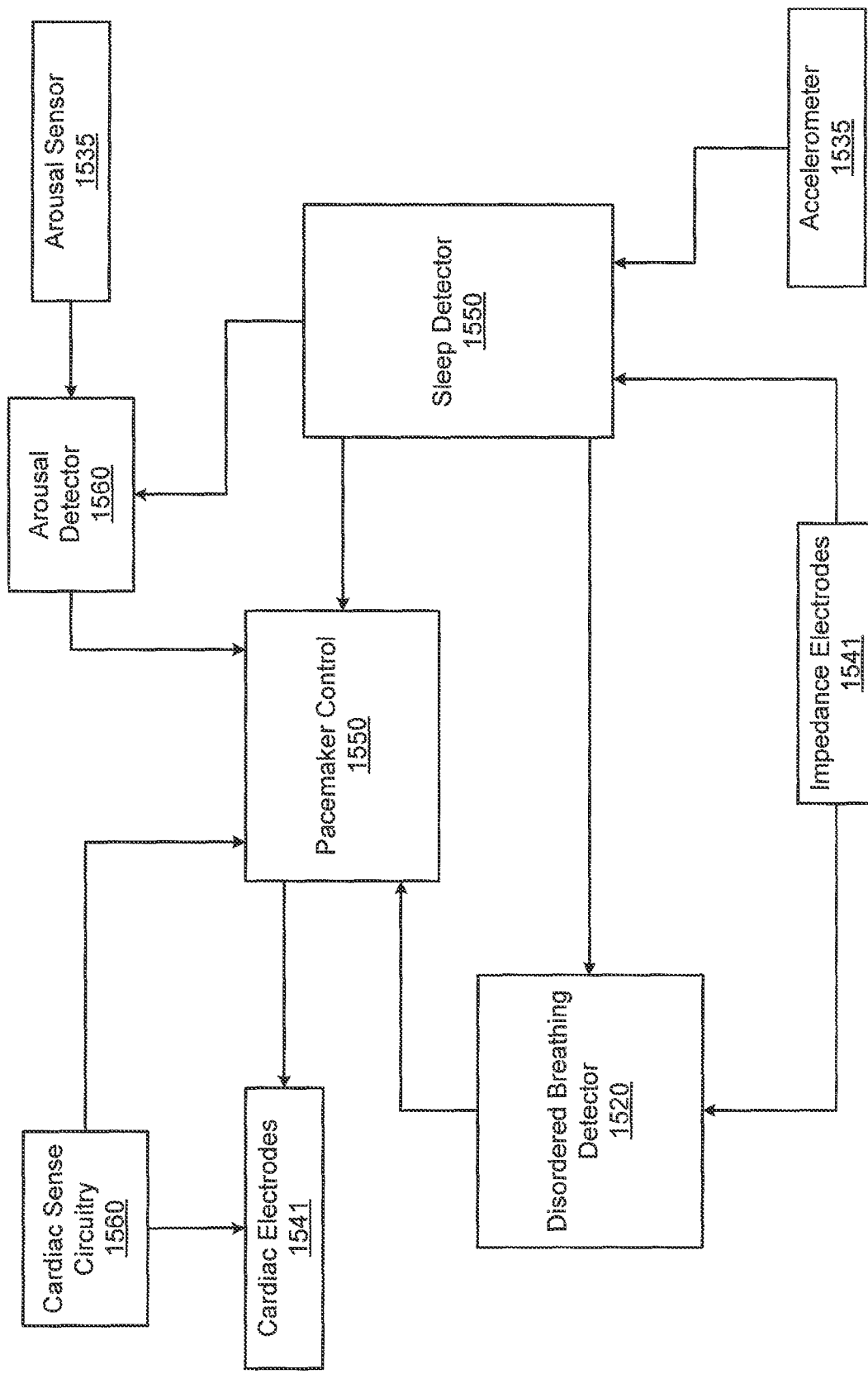
FIG. 15 is a block diagram of a cardiac rhythm management (CRM) system suitable for implementing an arousal detection methodology in accordance with embodiments of the present invention.

FIG. 15 is a block diagram of an arousal detection system that is implemented in cooperation with a cardiac rhythm management (CRM) system such as a pacemaker and/or cardioverter/defibrillator in accordance with an embodiment of the invention. The system may be completely implantable.

Cardiac sense circuitry 1560, cardiac therapy unit 1555, disordered breathing detector 1520, arousal detector, 1565, and sleep detector 1550 are arranged within a housing that is hermetically sealed and suitable for implanting within the patient, such as in the pectoral region of the patient's chest. An accelerometer 1536, configured to detect patient activity, may also be incorporated within the housing. An arousal sensor 1535, e.g., an EMG sensor, is disposed on the housing so that the EMG sensor 1535 is positioned in contact with or near skeletal muscle, such as the pectoral muscle. An intracardiac lead system includes cardiac electrodes 1555 for electrically coupling to the patient's heart and one or more transthoracic impedance electrodes for generating a respiration signal.

The sleep detector uses the patient activity signal generated by the accelerometer 1536 and the respiration signal generated by the transthoracic impedance electrodes 1542 to determine if the patient is asleep or awake.

The disordered breathing detector detects disordered breathing events based on the patient's respiration patterns, as described more fully above. The arousal detector compares the EMG signal to a characteristic arousal signature and detects arousal based on the comparison. Disordered breathing detection and arousal detection may be enhanced using sleep/wake information provided by the sleep detector.

In one embodiment, the CRM provides cardiac electrical stimulation the to one or more heart chambers as therapy for disordered breathing. Various approaches to delivering cardiac electrical stimulation therapy for treatment of disordered breathing, some of which may be utilized connection with embodiments presented herein, are described in commonly owned U.S. patent application Ser. No. 10/643,203, filed Aug. 18, 2003, now U.S. Pat. No. 7,720,541 and incorporated herein by reference.

The therapy control unit 1555 may utilize signals from the sleep detector 1550, disordered breathing detector 1520, and arousal detector 1565 to initiate, terminate, and/or adjust the cardiac electrical stimulation therapy for disordered breathing. For example, the therapy control unit 1555 may initiate a process for treating disordered breathing episodes when the sleep detector 1550 determines that the patient is asleep.

In one scenario, the therapy control unit 1555 may initiate cardiac electrical stimulation, e.g., cardiac overdrive pacing, to treat disordered breathing upon detection of a disordered breathing event during sleep. In another scenario, the therapy control unit 1555 may initiate cardiac electrical stimulation to treat disordered breathing when sleep is detected. The therapy control unit 1555 may adjust the cardiac electrical stimulation when a disordered breathing event is detected during sleep. If an arousal is detected, then the therapy control unit 1555 may terminate or adjust the cardiac electrical stimulation therapy for disordered breathing. Adjustment of the cardiac electrical stimulation therapy may involve increasing the pacing rate, initiating multi-site pacing, switching the cardiac pacing from one site to another site. The pacing mode may be switched to a pacing mode that promotes atrial pacing, or promotes consistent ventricular pacing. The pacing mode may be switched from single chamber to multiple chambers, or the reverse. For example, a bi-ventricular mode may be switched to a left ventricular mode only. Alternatively, a single chamber mode, e.g., LV or RV, may be switched to a bi-ventricular mode. Other adjustments are also possible.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The functional blocks may be implemented, for example, in hardware, software, or a combination of hardware and software. The examples depicted herein provide examples of possible functional arrangements used to implement the approaches of the present invention.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Accordingly, it is intended that the invention be limited only by the scope of the appended claims.

What is claimed is:

1. A method for adjusting a patient neurostimulation therapy, comprising:
sensing one or more physiological conditions modulated by a patient's autonomic arousal response;
detecting autonomic arousal events occurring during sleep based on the one or more sensed physiological conditions, wherein at least one of sensing the physiological conditions and detecting the autonomic arousal events is performed at least in part implantably;
discriminating between autonomic arousal events associated with sleep disorder events and autonomic arousal events not associated with sleep disorder events; and
adjusting the patient neurostimulation therapy based, at least in part, on the discriminated autonomic arousal events.

2. The method according to claim 1, wherein the patient therapy further comprises a cardiac stimulation therapy, and wherein the method further comprises adjusting the patient cardiac stimulation therapy based, at least in part, on the discriminated autonomic arousal events.

3. The method according to claim 1, wherein the patient therapy further comprises a hypertension therapy, and wherein the method further comprises adjusting the patient hypertension therapy based, at least in part, on the discriminated autonomic arousal events.

4. The method according to claim 1, wherein only autonomic arousal events not associated with sleep disorder events are used in adjusting the neurostimulation therapy.

5. The method of claim 1 wherein the autonomic arousal events are detected by observing an output of an EMG sensor configured to generate a signal modulated with changes in muscle tone associated with autonomic arousal events.

6. A method for monitoring a patient therapy, comprising:
sensing one or more physiological conditions modulated by a patient's autonomic arousal response;
detecting autonomic arousal events occurring during sleep based on the one or more sensed physiological conditions, wherein at least one of sensing the physiological conditions and detecting the autonomic arousal events is performed at least in part implantably; and
discriminating between autonomic arousal events associated with sleep disorder events and autonomic arousal events not associated with sleep disorder events; and
monitoring a patient therapy based at, least in part, on the discrimination of the autonomic arousal events.

7. The method according to claim 6, further comprising adjusting the patient therapy based, at least in part, on the detected autonomic arousal events.

8. The method according to claim 6, wherein the patient therapy comprises a neural stimulation therapy.

9. The method according to claim 6, wherein:
sensing the one or more physiological conditions comprises sensing sympathetic nerve activity; and
detecting the autonomic arousal events is based at least in part on the sensed sympathetic nerve activity.

10. The method according to claim 6, wherein the patient therapy comprises a therapy for treating hypertension.

11. The method according to claim 6, further comprising:
determining a trend of the autonomic arousal events; and
using the autonomic arousal event trend to monitoring the patient therapy.

12. The method according to claim 6, wherein:
sensing the one or more physiological conditions comprises sensing heart rate; and
detecting the autonomic arousal events comprises:
determining heart rate variability based on the sensed heart rate; and
detecting one or more of the autonomic arousal events based at least in part on the heart rate variability.

13. The method according to claim 6, wherein:
sensing the one or more physiological conditions comprises sensing at least one physiological condition that is modulated contemporaneously with an occurrence of an autonomic arousal event; and
detecting the autonomic arousal events comprises detecting the autonomic arousal events contemporaneously with modulation of the physiological condition.

14. A medical system for monitoring a patient therapy comprising:
one or more sensors configured to sense one or more physiological conditions associated with a patient's autonomic arousal response;
an implantable arousal detector coupled to the one or more sensors, the arousal detector configured to detect autonomic arousal events based on the one or more physiological conditions; and
a controller operatively coupled to the arousal detector, the controller configured to discriminate between autonomic arousal events associated with sleep disorder events and autonomic arousal events not associated with sleep disorder events, and to monitor the patient therapy based at, least in part, on the discriminated autonomic arousal events.

15. The medical system of claim 14 further comprising:
a therapy unit, operatively coupled to the controller, configured to adjust the patient therapy based, at least in part, on the discriminated autonomic arousal events.

16. The medical system of claim 15, wherein the therapy unit is configured to deliver a neurostimulation therapy to the patient, and is further configured to adjust the neurostimulation therapy based, at least in part, on the discriminated autonomic arousal events.

17. The medical system of claim 15, wherein the therapy unit is configured to deliver a cardiac electrical stimulation therapy to the patient, and is further configured to adjust the cardiac electrical stimulation therapy based, at least in part, on the discriminated autonomic arousal events.

18. The medical system of claim 15, wherein the therapy unit is configured to deliver a therapy to treat hypertension in the patient, and is further configured to adjust the therapy based, at least in part, on the discriminated autonomic arousal events.

19. The medical system of claim 14, wherein the controller is configured to determine a trend of the detected autonomic arousal events, and to use the autonomic arousal event trend to monitoring the patient therapy.

20. The medical system of claim 14, wherein the controller is configured to determine an arousal event index based on the detected autonomic arousal events, and to monitor the patient therapy based on the index.

* * * * *